(12) United States Patent
Dyatkin et al.

(10) Patent No.: US 9,184,399 B2
(45) Date of Patent: Nov. 10, 2015

(54) ASYMMETRIC HOSTS WITH TRIARYL SILANE SIDE CHAINS

(75) Inventors: Alexey Dyatkin, Ambler, PA (US); Lichang Zeng, Lawrenceville, NJ (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 840 days.

(21) Appl. No.: 13/464,122

(22) Filed: May 4, 2012

(65) Prior Publication Data

US 2013/0293094 A1 Nov. 7, 2013

(51) Int. Cl.
*H01L 51/50* (2006.01)
*H01L 51/00* (2006.01)
*C07F 7/08* (2006.01)

(52) U.S. Cl.
CPC .......... *H01L 51/0094* (2013.01); *C07F 7/0812* (2013.01); *C07F 7/0814* (2013.01); *H01L 51/0073* (2013.01); *H01L 51/0054* (2013.01); *H01L 51/50* (2013.01)

(58) Field of Classification Search
None
See application file for complete search history.

(56) References Cited

U.S. PATENT DOCUMENTS

| 4,769,292 | A | 9/1988 | Tang et al. |
|---|---|---|---|
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |

(Continued)

FOREIGN PATENT DOCUMENTS

| EP | 0650955 | 5/1995 |
|---|---|---|
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Gregory Clark
(74) *Attorney, Agent, or Firm* — Duane Morris LLP

(57) ABSTRACT

Novel asymmetric host compounds containing an electron-transport moiety, a hole-transport moiety, an aromatic spacer, and a triaryl silane group are provided. These compounds are useful materials that can be incorporated into OLED devices.

27 Claims, 4 Drawing Sheets

(56) References Cited

U.S. PATENT DOCUMENTS

| | | |
|---|---|---|
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Hueschen |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106106 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1* | 1/2009 | Iwakuma et al. ............ 544/251 |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0219403 A1* | 9/2010 | Langer et al. ............... 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3 , 2007.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

(56) References Cited

OTHER PUBLICATIONS

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett. 77(15)2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5''-Bis(dimesitylboryl)-2,2'5',2''-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto,Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett, 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

| LiF/Al 1000 A |
|---|
| Alq 400 A |
| BL 50 A |
| Compound/dopant 205 300A |
| NPD |
| LG101 |
| ITO 800A |

FIGURE 3

Compound 1

ASYMMETRIC HOSTS WITH TRIARYL SILANE SIDE CHAINS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to molecules containing an electron-transport moiety, a hole-transport moiety, a spacer moiety, and a triaryl silane group. These molecules are useful as host compounds in phosphorescent OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

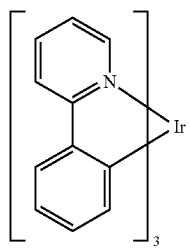

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest. Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In one aspect, a compound having the formula:

$$L_1\text{-}L_2\text{-}L_3 \quad \text{Formula I}$$

is provided. In the compound of Formula I, $L_1$ is selected from the group consisting of carbazole, azacarbazole, triphenylene, aza-triphenylene and combinations thereof, $L_2$ is selected from the group consisting of phenyl, pyridine, pyrazine, triazine and combinations thereof; and $L_3$ is selected from the group consisting of dibenzofuran, dibenzothiophene, azadibenzofuran, azadibenzothiophene, dibenzoselenophene, azadibenzoselenophene, and combinations thereof. At least one of $L_1$ to $L_3$ is substituted by at least one $SiAr_1Ar_2Ar_3$ group, where $Ar_1$ to $Ar_3$ are independently selected from aryl or heteroaryl groups. Each of $L_1$ to $L_3$ is optionally substituted with a group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any optional substitution on $L_1$ and $L_3$ can be fused to $L_1$ and $L_3$ respectively, whereas any optional substitution on $L_2$ is unfused.

In one aspect, each of $L_1$ to $L_3$ is optionally substituted with a group selected from the group consisting of hydrogen, deuterium, aryl, heteroaryl, or combinations thereof. In one aspect, each of $L_1$ to $L_3$ is substituted with hydrogen.

In one aspect, $L_1$ is selected from the group consisting of:

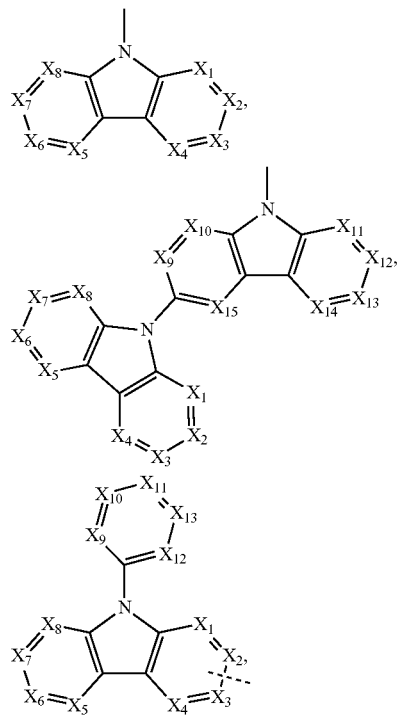

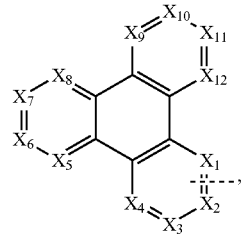

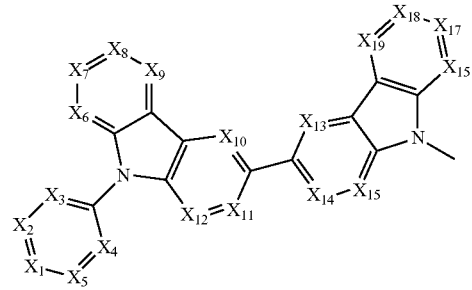

In one aspect, $X_1$ to $X_{19}$ are independently CR or N, wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $L_1$ is selected from the group consisting of

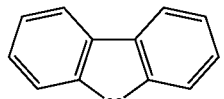 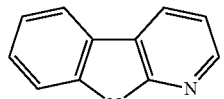

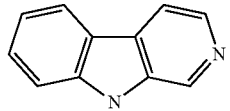 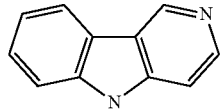

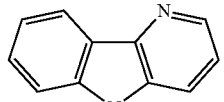 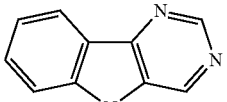

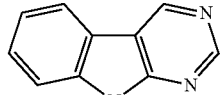 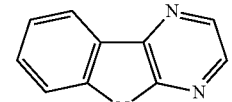

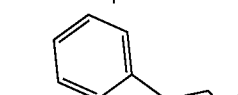 

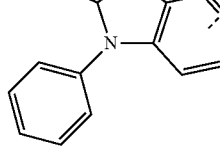

-continued
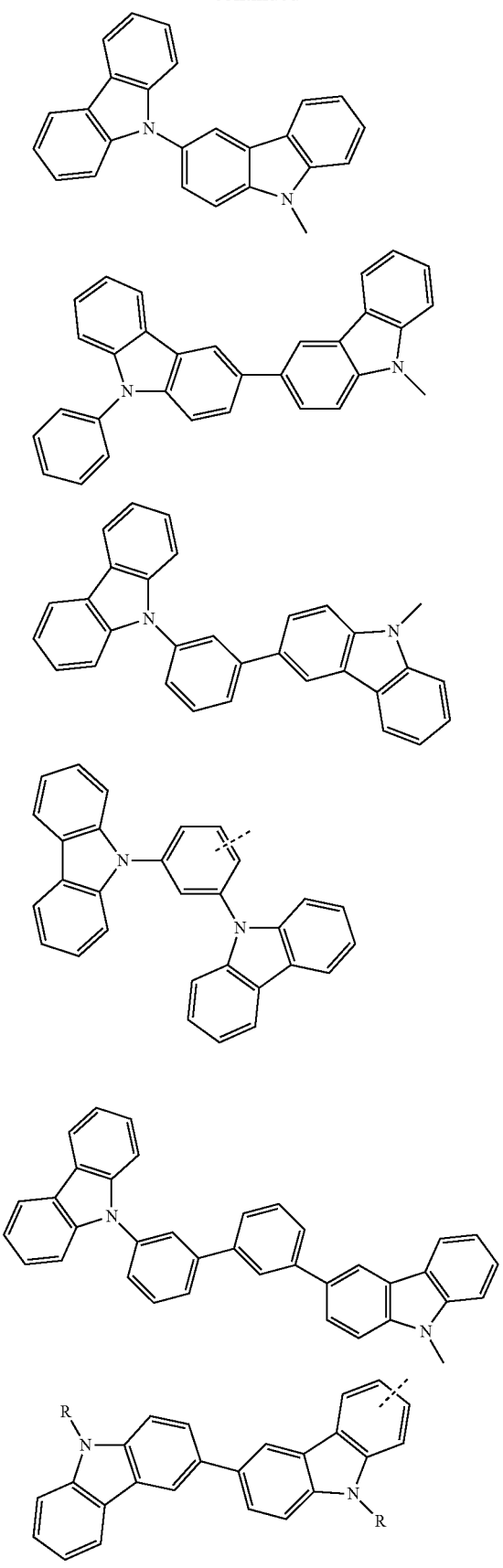
-continued
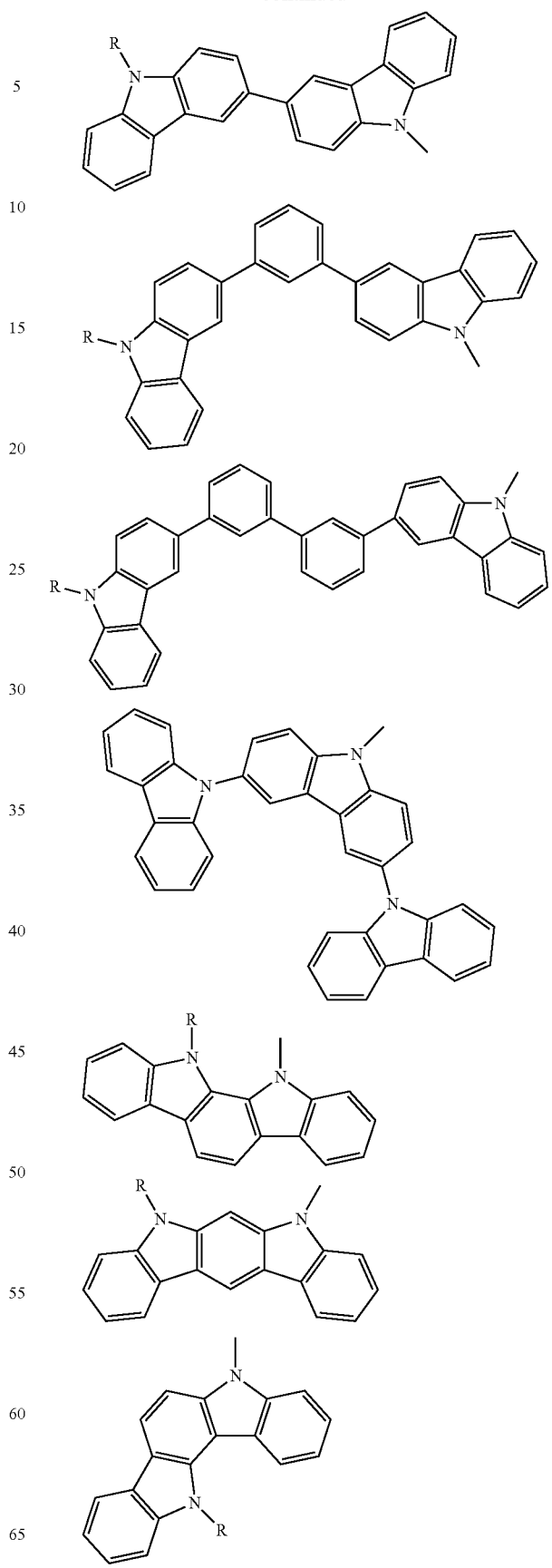

-continued

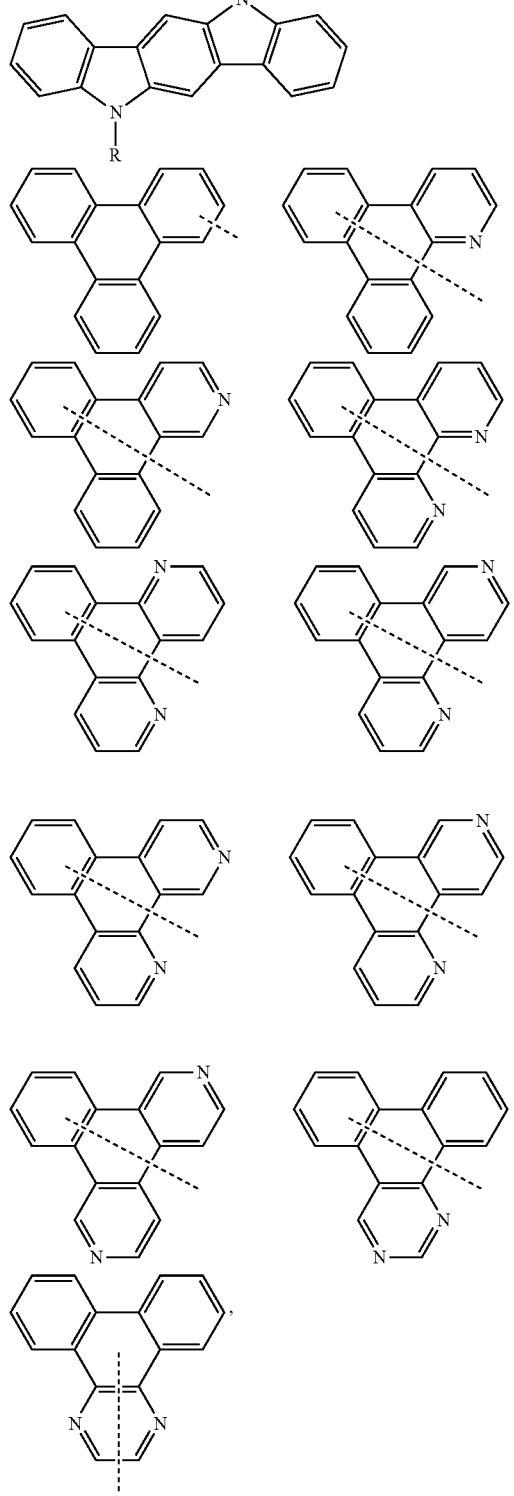

wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof.

In one aspect, $L_2$ is selected from the group consisting of:

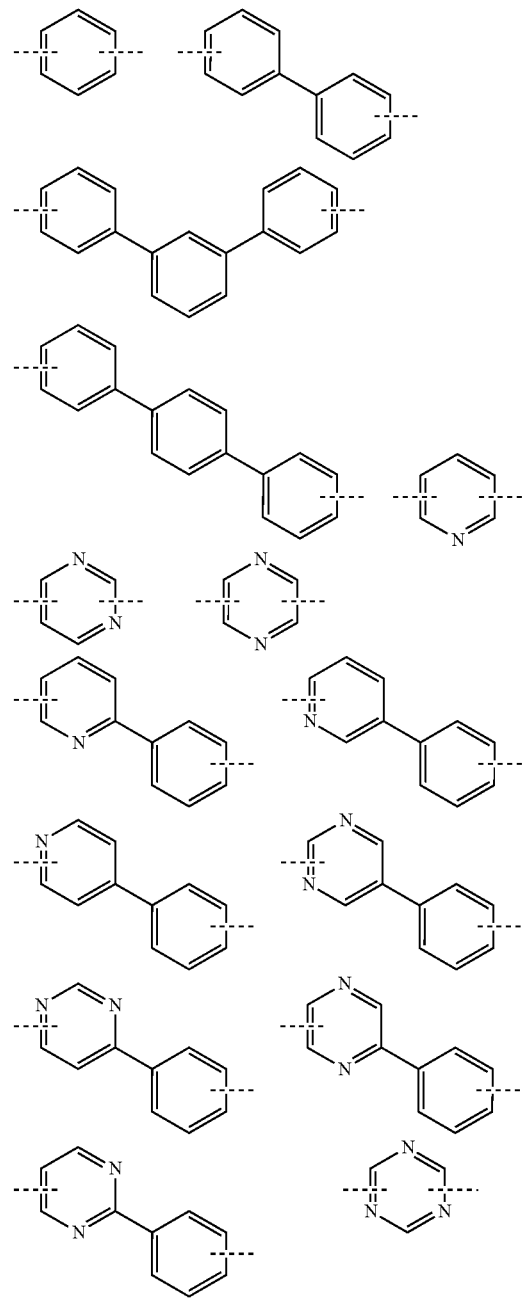

In one aspect, $L_3$ is selected from the group consisting of:

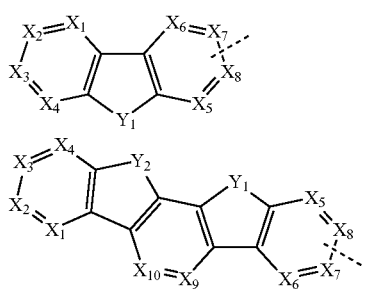

-continued

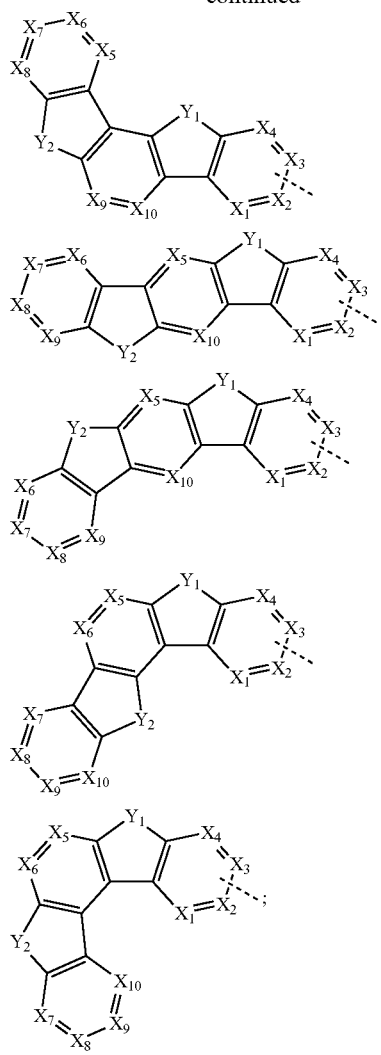

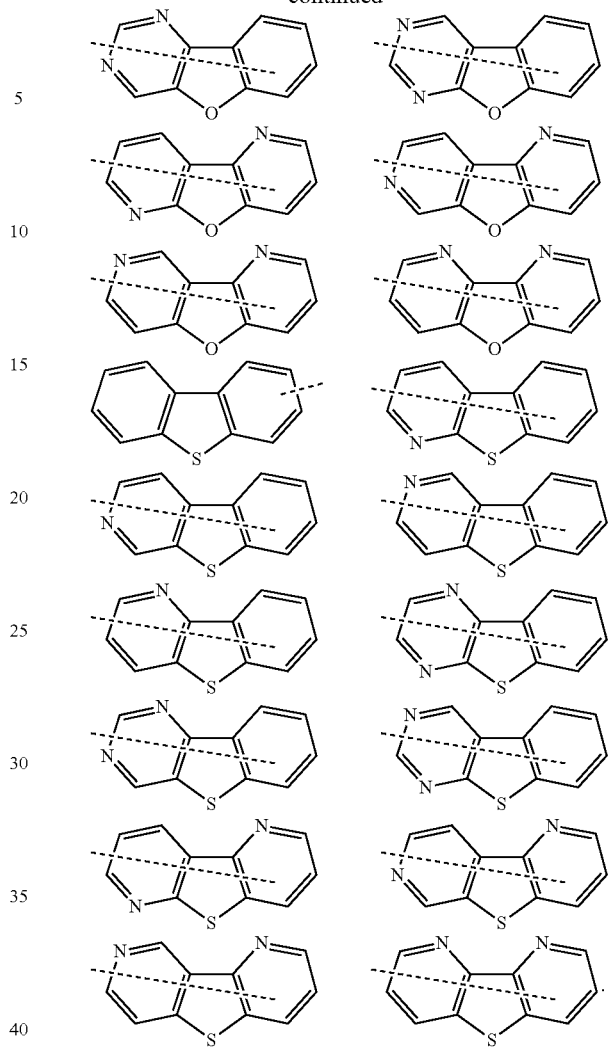

wherein $X_1$ to $X_{10}$ are independently CR or N, $Y_1$ and $Y_2$ are independently O, S, or Se, and R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $L_3$ is selected from the group consisting of:

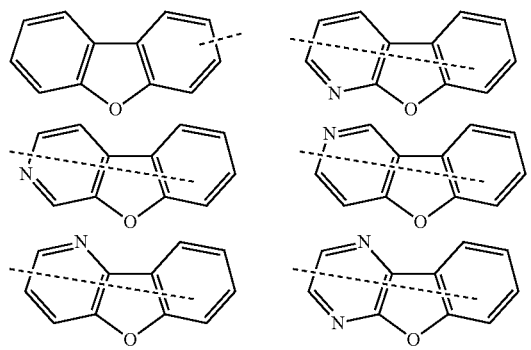

In one aspect, $Ar_1$ to $Ar_3$ are selected from the group consisting of phenyl, biphenyl, pyridyl, naphthyl, and combinations thereof. In one aspect, $Ar_1$, $Ar_2$, and $Ar_3$ are phenyl.

In one aspect, $L_3$ contains dibenzothiophene. In one aspect, $L_3$ contains dibenzofuran.

In one aspect, $L_2$ contains phenyl. In one aspect, $L_2$ contains a biphenyl. In one aspect, $L_2$ contains a terphenyl.

In one aspect, $L_1$ contains carbazole. In one aspect, $L_1$ contains triphenylene.

In one aspect, the compound is selected from the group consisting of Compound 1-Compound 18.

In one aspect, a first device is provided. The first device comprises an organic light emitting device, further comprising an anode, a cathode, and an organic layer, disposed between the anode and the cathode, comprising a compound having the formula:

$$L_1\text{-}L_2\text{-}L_3 \qquad \text{Formula I}$$

In the compound of Formula I, $L_1$ is selected from the group consisting of carbazole, azacarbazole, triphenylene, aza-triphenylene and combinations thereof, $L_2$ is selected from the group consisting of phenyl, pyridine, pyrazine, triazine and combinations thereof, and $L_3$ is selected from the group consisting of dibenzofuran, dibenzothiophene, azadibenzofuran, azadibenzothiophene, dibenzoselenophene, azadibenzoselenophene, and combinations thereof. At least one of $L_1$ to $L_3$ is substituted by at least one $SiAr_1Ar_2Ar_3$ group, where $Ar_1$ to $Ar_3$ are independently selected from aryl or heteroaryl groups. Each of $L_1$ to $L_3$ is optionally substituted with a group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any optional substitution on $L_1$ and $L_3$ can be fused to $L_1$ and $L_3$ respectively, whereas any optional substitution on $L_2$ is unfused.

In one aspect, the organic layer is an emissive layer and the compound of Formula I is a host.

In one aspect, the first device further comprises a first dopant material that is an emissive dopant comprising a transition metal complex having at least one ligand or part of the ligand if the ligand is more than bidentate selected from the group consisting of:

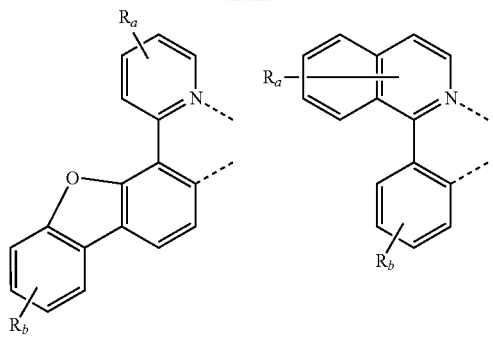

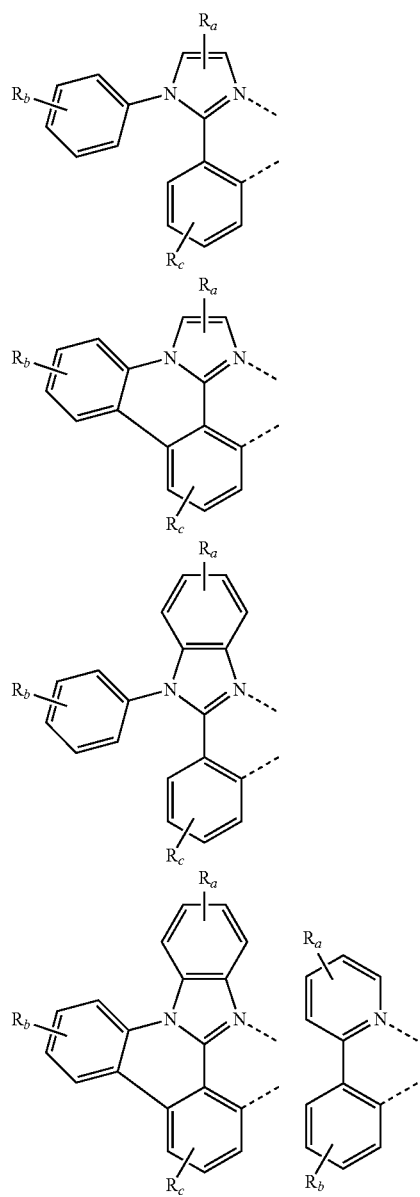

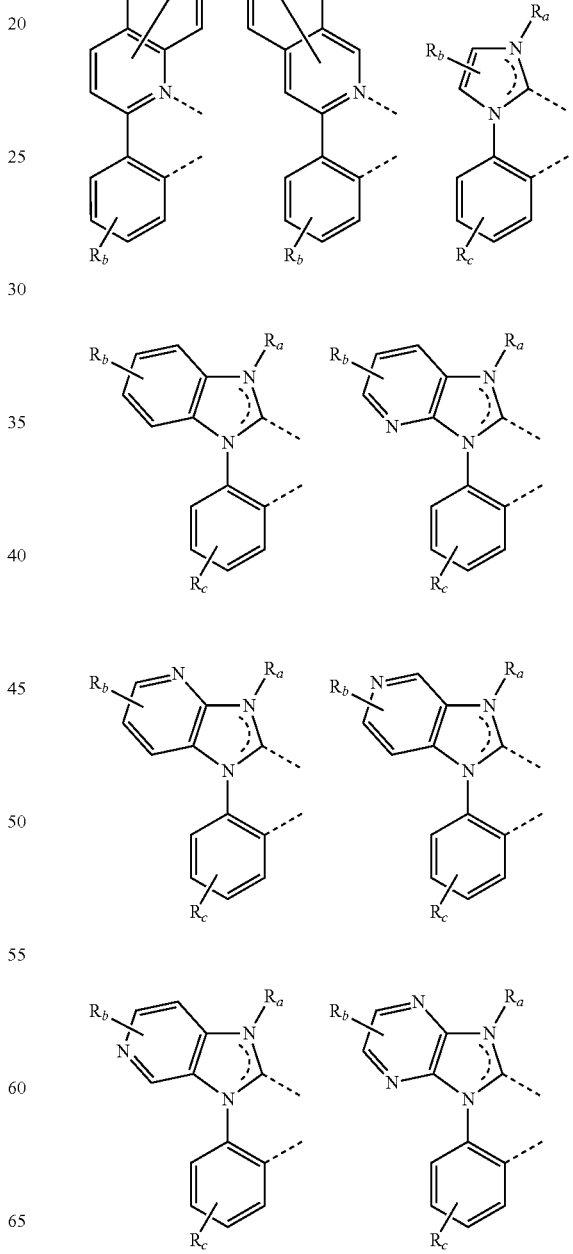

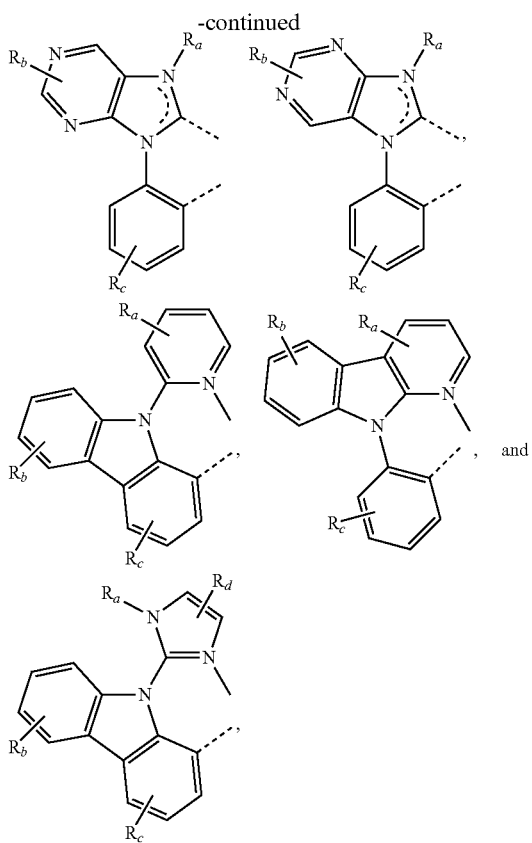

wherein $R_a$, $R_b$, $R_c$ and $R_d$ may represent mono, di, tri, or tetra substitution, or no substitution, and $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In one aspect, the organic layer is a non-emissive layer. In one aspect, the organic layer is a first organic layer, and the device further comprises a second organic layer that is a non-emissive layer and the compound having Formula I is a material in the second organic layer.

In one aspect, the second organic layer is a blocking layer and the compound having Formula I is a blocking material in the second organic layer. In one aspect, the first device is a consumer product. In one aspect, the first device is an organic light-emitting device. In one aspect, the first device comprises a lighting panel.

BRIEF DESCRIPTION OF THE DRAWINGS

FIG. 3 shows an exemplary device configuration incorporating compounds of Formula I.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electraluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
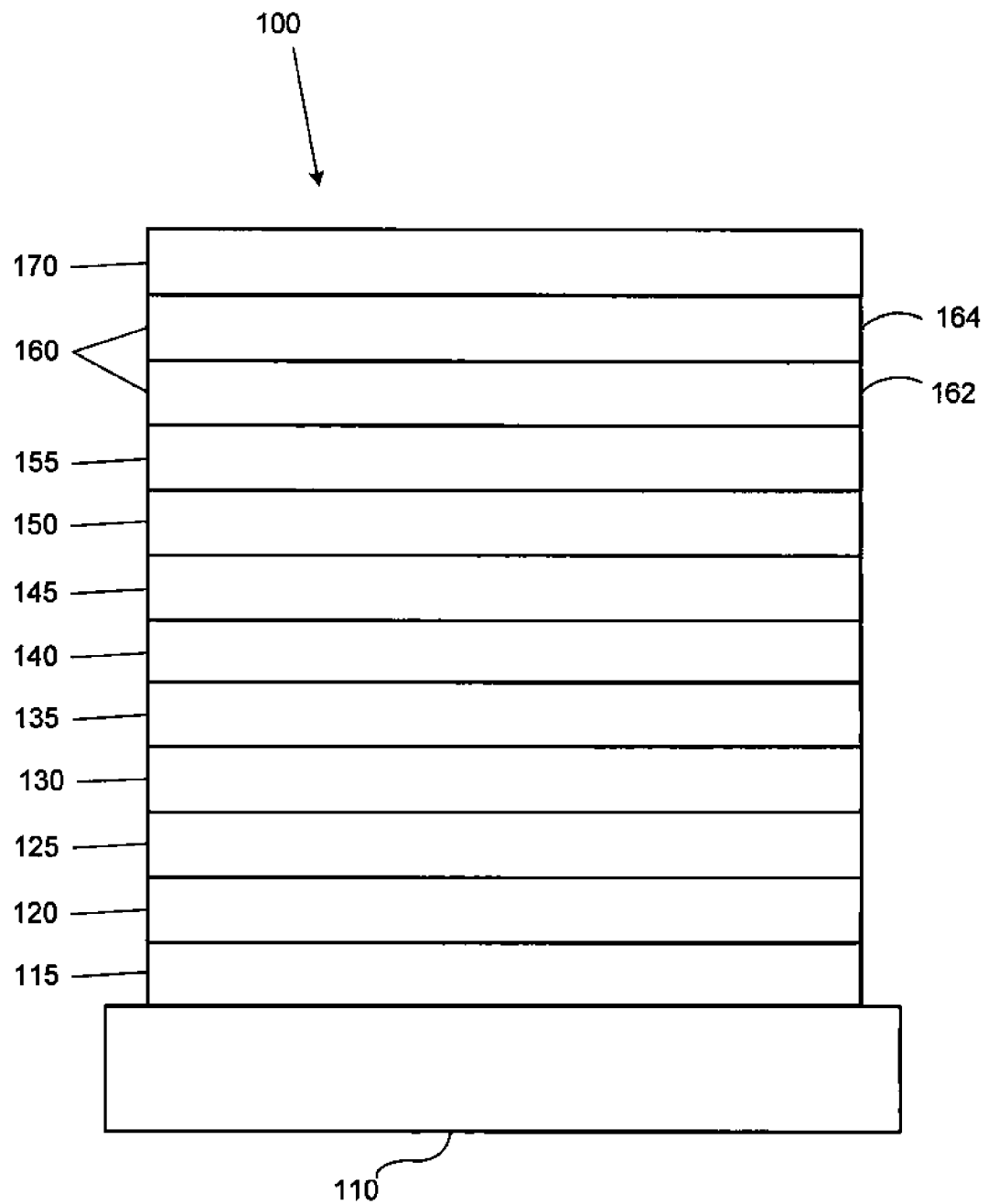
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
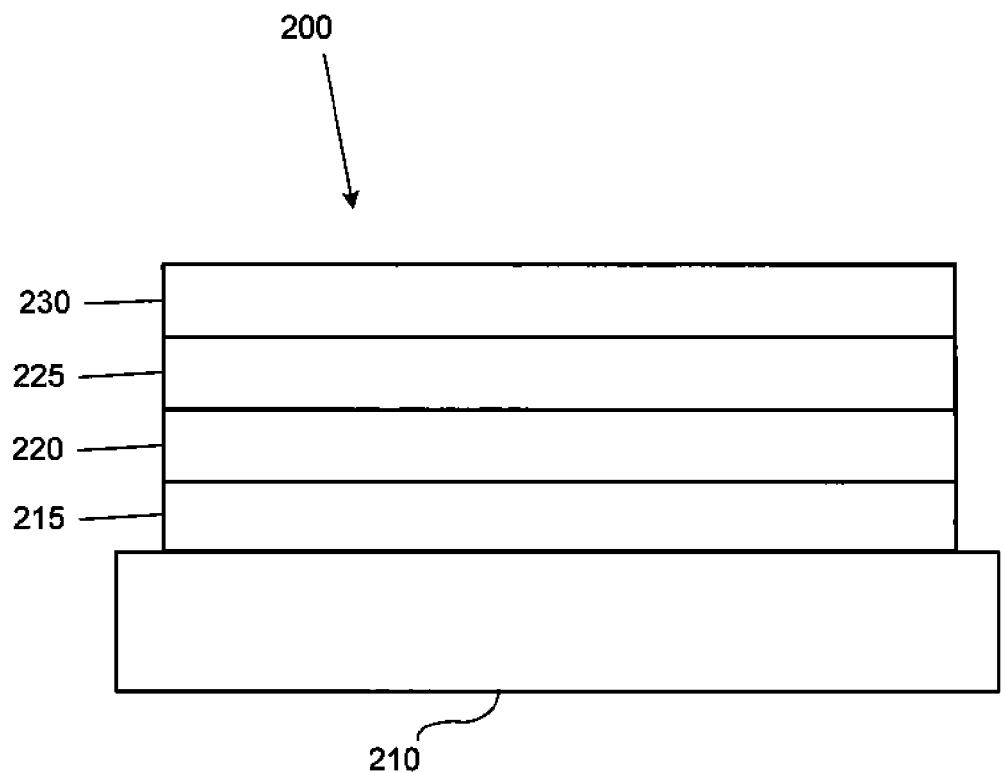
FIG. 2 shows an inverted organic light emitting device that does not have a separate electron transport layer.
Figure 4:
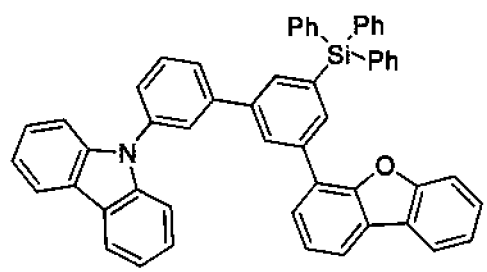
FIG. 4 shows an exemplary compound according to Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In one embodiment, a compound having the formula:

$$L_1\text{-}L_2\text{-}L_3 \qquad \text{Formula I}$$

is provided. In the compound of Formula I, $L_1$ is selected from the group consisting of carbazole, azacarbazole, triphenylene, aza-triphenylene and combinations thereof, $L_2$ is selected from the group consisting of phenyl, pyridine, pyrazine, triazine and combinations thereof, and $L_3$ is selected from the group consisting of dibenzofuran, dibenzothiophene, azadibenzofuran, azadibenzothiophene, dibenzoselenophene, azadibenzoselenophene, and combinations thereof. At least one of $L_1$ to $L_3$ is substituted by at least one $SiAr_1Ar_2Ar_3$ group, where $Ar_1$ to $Ar_3$ are independently selected from aryl or heteroaryl groups. Each of $L_1$ to $L_3$ is optionally substituted with a group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any optional substitution on $L_1$ and $L_3$ can be fused to $L_1$ and $L_3$ respectively, whereas any optional substitution on $L_2$ is unfused.

In $L_2$, the fragments listed above can appear more than once and in any combination, so that, for example, $L_2$ can comprise two phenyl units (i.e. biphenyl), three phenyl units (i.e. terphenyl), two pyridines (i.e. bipyridine), a phenyl and a pyridine, etc. The groups in $L_1$, $L_2$, and $L_3$ can have multiple attachment points connecting them to other fragments.

The "aza" designation in the fragments described above, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofurna). As used herein, these different ways of designating a substituent or attached fragment are considered to be equivalent.

The term "fused," as used herein to refer to substituents on $L_1$, $L_2$, or $L_3$ means that the substitution on $L_1$, $L_2$, or $L_3$ is also attached to least at one other ring-atom on the ring bearing that substitution. The term "unfused," as used herein to refer to substituents on $L_1$, $L_2$, or $L_3$ means that the substitution on $L_1$, $L_2$, or $L_3$ is not attached to any other ring-atom in the ring bearing that substitution.

It has been discovered that incorporation of both electron- and hole-transport moieties into one compound fine-tunes the energy levels, facilitates charge injection from adjacent layers to suppress driving voltage, and balances electron/hole fluxes and modulates charge trapping by the emitter dopant to achieve an expanded recombination zone. The $L_2$ spacer provides one additional region of substitution to further adjust the molecular assembly and charge transport properties. The triarylsilyl groups alleviate the undesirable intermolecular stacking, which not only retains high triplet energy in the solid state and effectively reduces quenching but also suppresses crystallization and improves film quality. The unique synergistic combination of all these properties is highly beneficial for host materials used in high-efficiency and stable phosphorescent OLED. Furthermore, the proposed compounds are soluble in common solvents such as xylene and toluene, amenable for solution processing which is highly desirable for potential low cost fabrication.

In one embodiment, each of $L_1$ to $L_3$ is optionally substituted with a group selected from the group consisting of hydrogen, deuterium, aryl, heteroaryl, or combinations thereof. In one embodiment, each of $L_1$ to $L_3$ is substituted with hydrogen.

In one embodiment, $L_1$ is selected from the group consisting of:

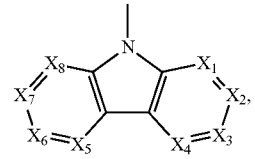

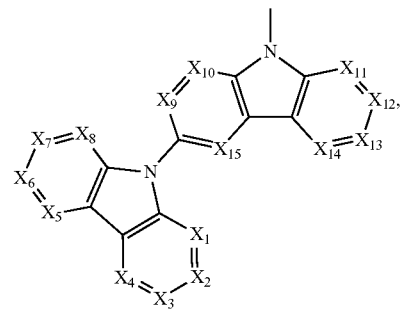

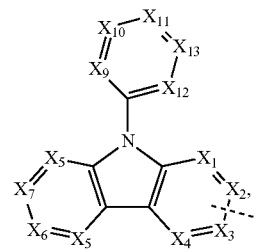

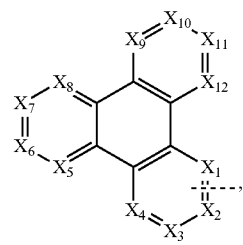

-continued

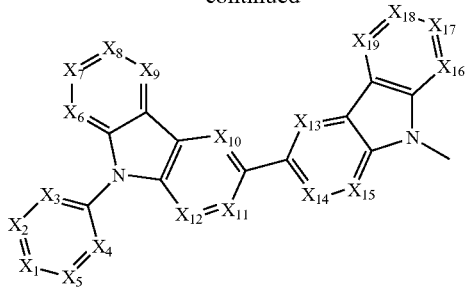

$X_1$ to $X_{19}$ are independently CR or N, wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, $L_1$ is selected from the group consisting of:

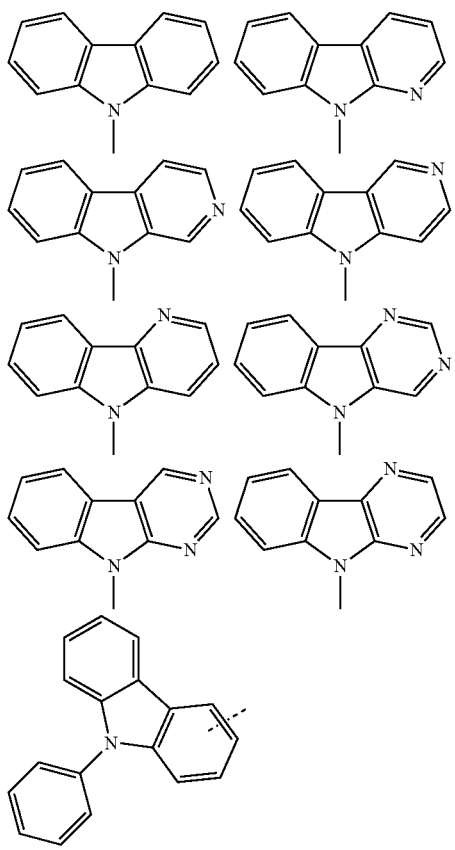

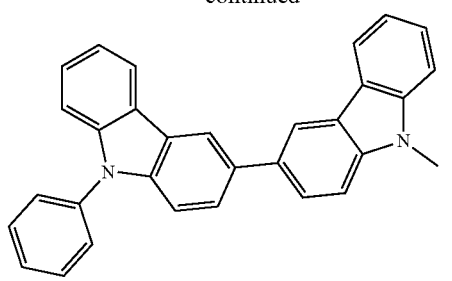

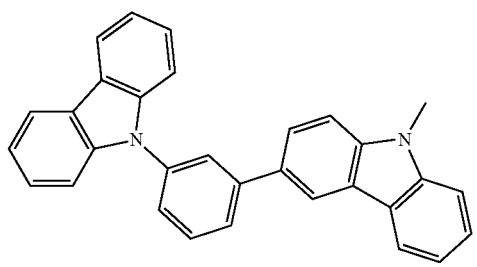

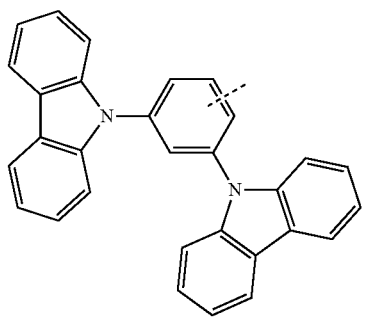

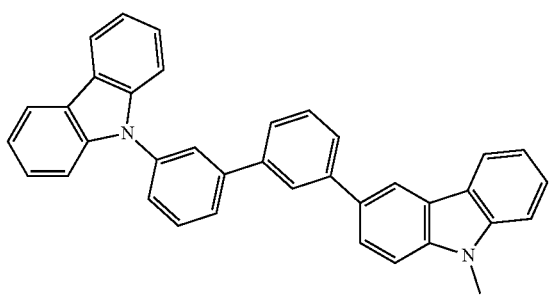

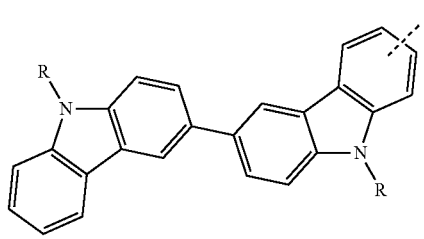

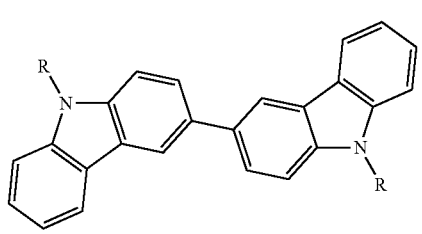

-continued

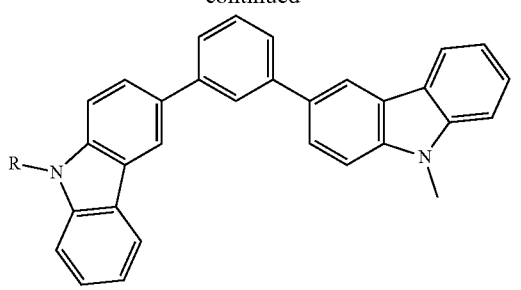

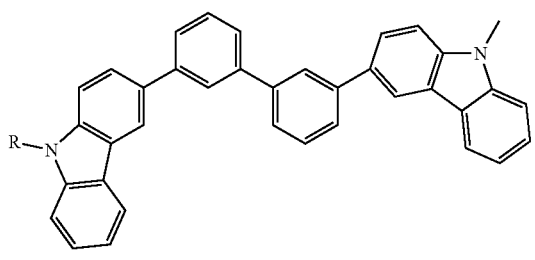

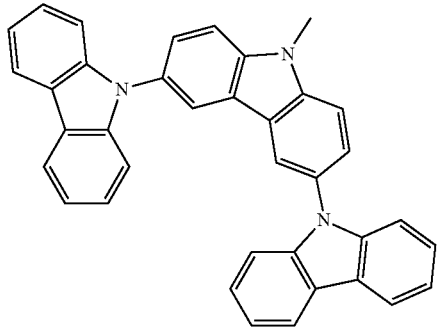

wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In any of the fragments disclosed herein, a dashed line indicates that that particular fragment can be attached at any position or positions on that fragment that has an open valence and is capable of forming a bond or bonds.

In one embodiment, $L_2$ is selected from the group consisting of:

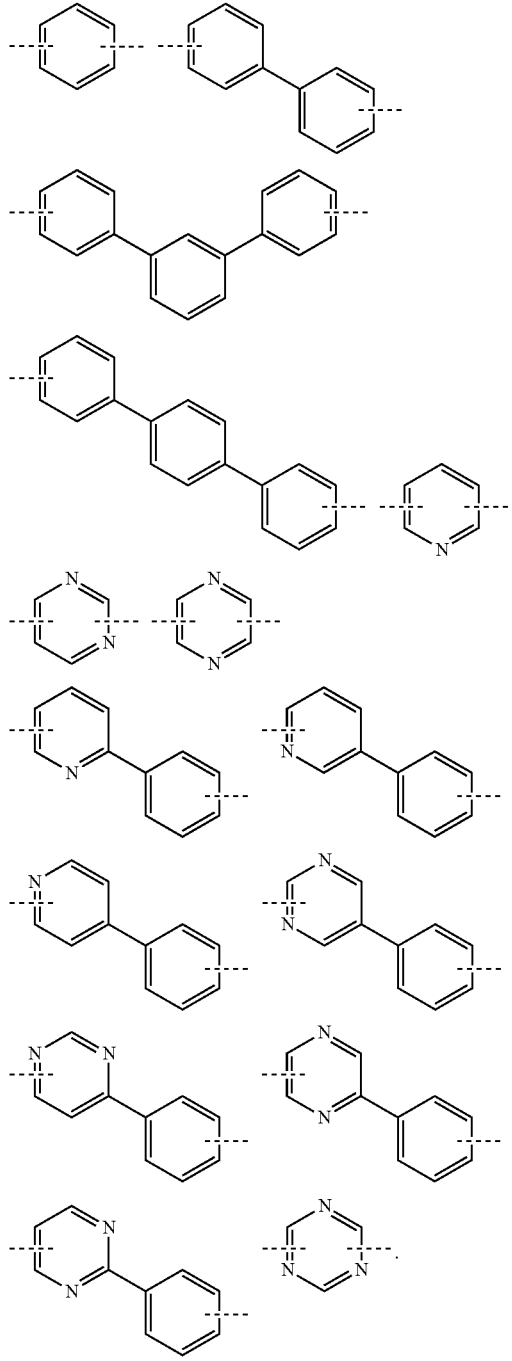

In one embodiment, $L_3$ is selected from the group consisting of

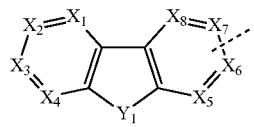

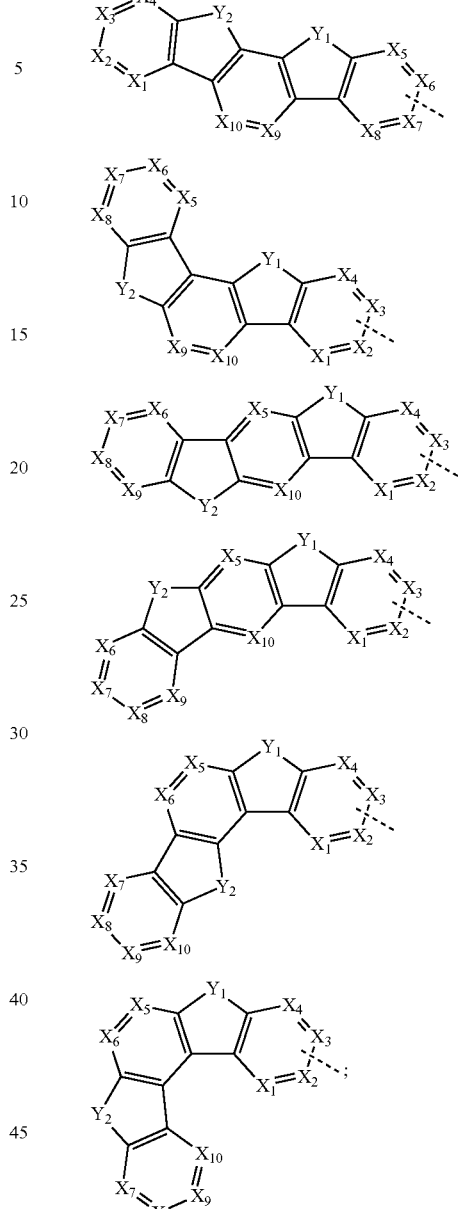

wherein $X_1$ to $X_{10}$ are independently CR or N, $Y_1$ and $Y_2$ are independently O, S, or Se, and R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof.

In one embodiment, $L_3$ is selected from the group consisting of:

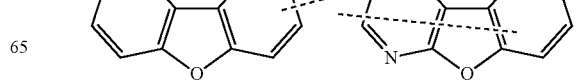

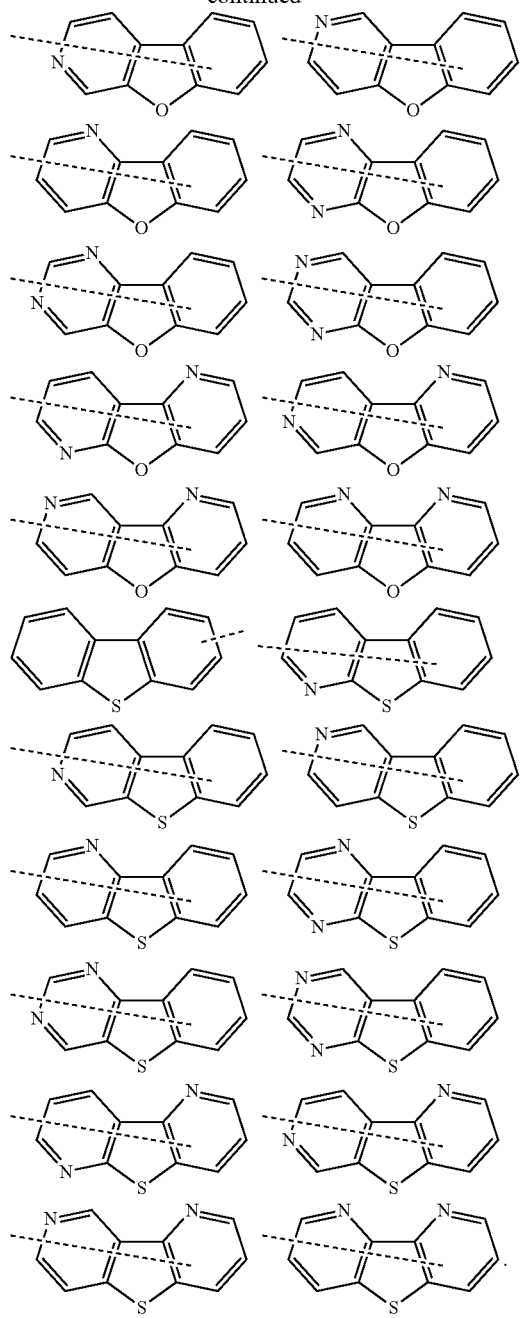

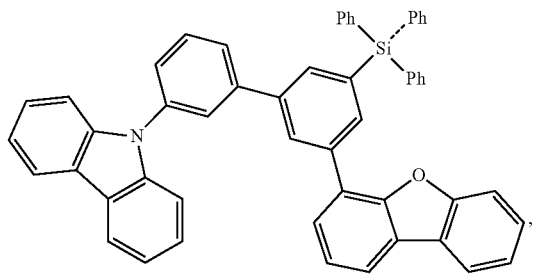

Compound 1

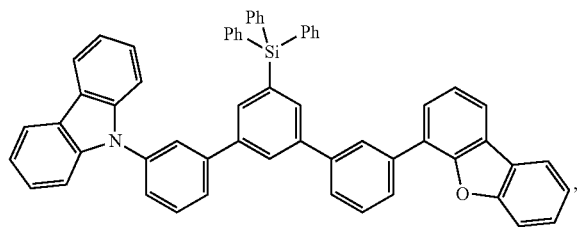

Compound 2

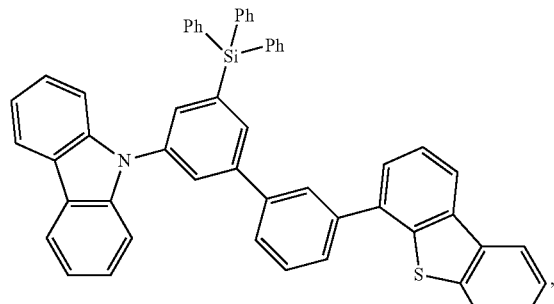

Compound 3

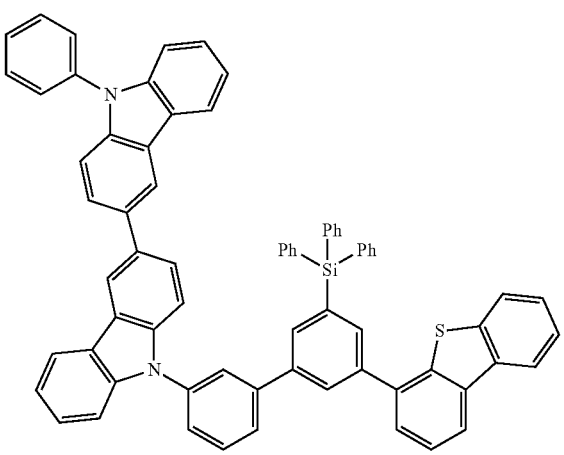

Compound 4

In one embodiment, $Ar_1$ to $Ar_3$ are selected from the group consisting of phenyl, biphenyl, pyridyl, naphthyl, and combinations thereof. In one embodiment, $Ar_1$, $Ar_2$, and $Ar_3$ are phenyl.

In one embodiment, $L_3$ contains dibenzothiophene. In one embodiment, $L_3$ contains dibenzofuran.

In one embodiment, $L_2$ contains phenyl. In one embodiment, $L_2$ contains a biphenyl. In one embodiment, $L_2$ contains a terphenyl.

In one embodiment, $L_1$ contains carbazole. In one embodiment, $L_1$ contains triphenylene.

In one embodiment, the compound is selected from the group consisting of Compound 1-Compound 18.

Compound 5
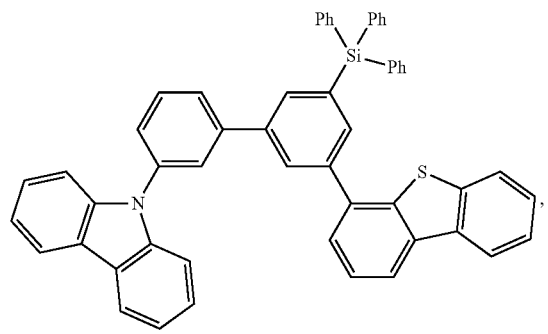
Compound 6
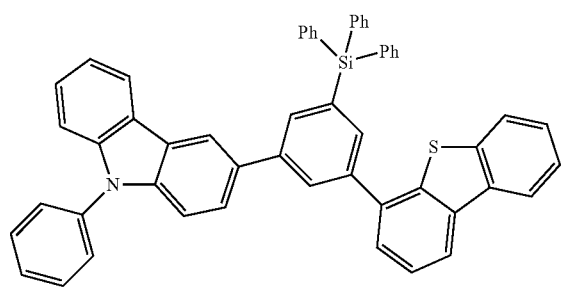
Compound 7
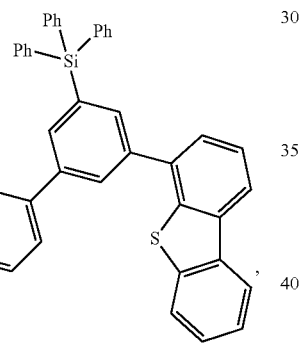
Compound 8
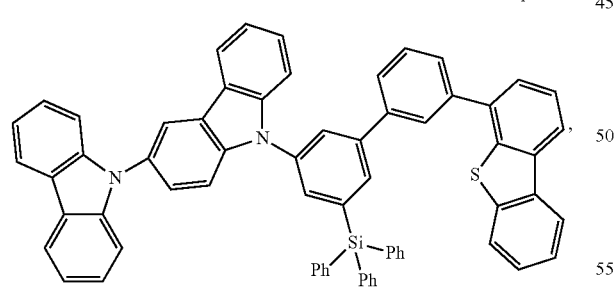
Compound 9
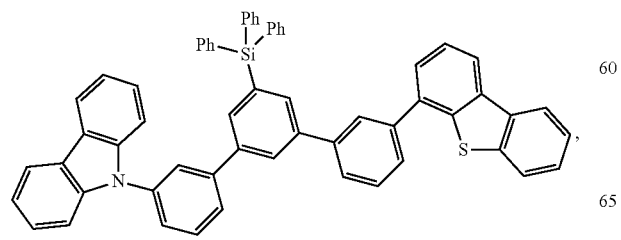
Compound 10
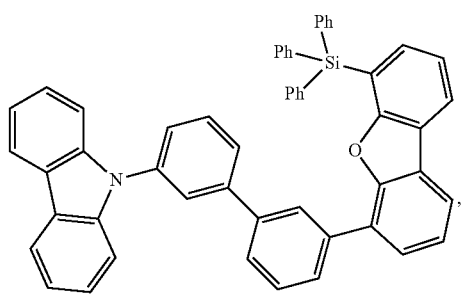
Compound 11
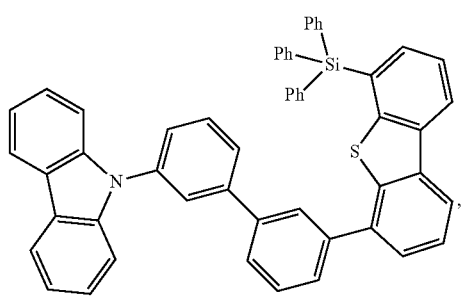
Compound 12
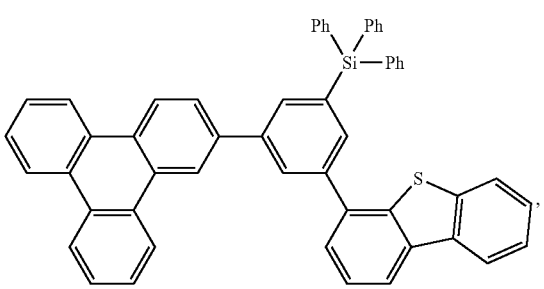
Compound 13
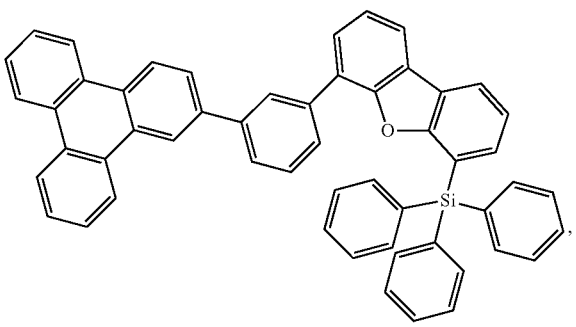

Compound 14
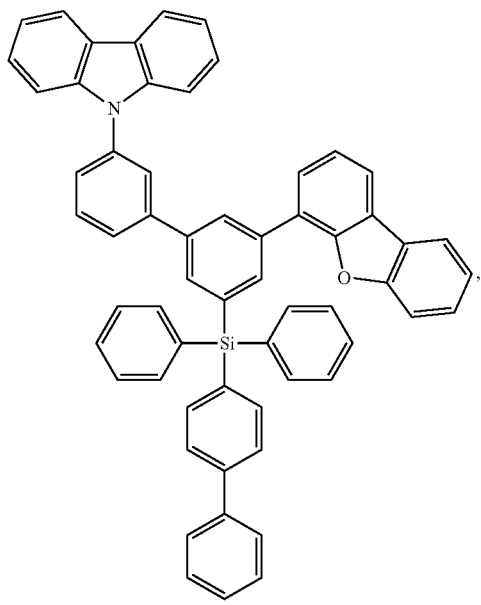
Compound 15
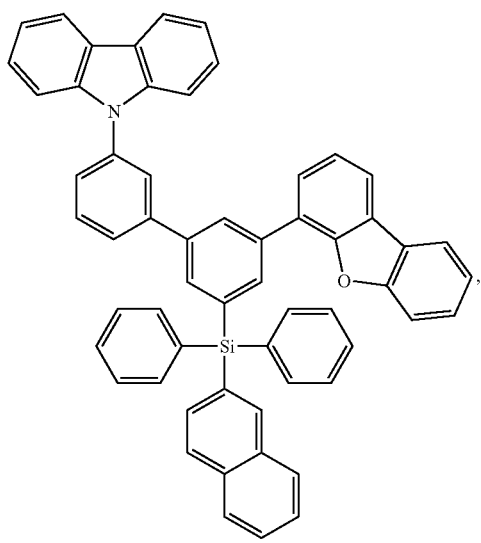
Compound 16
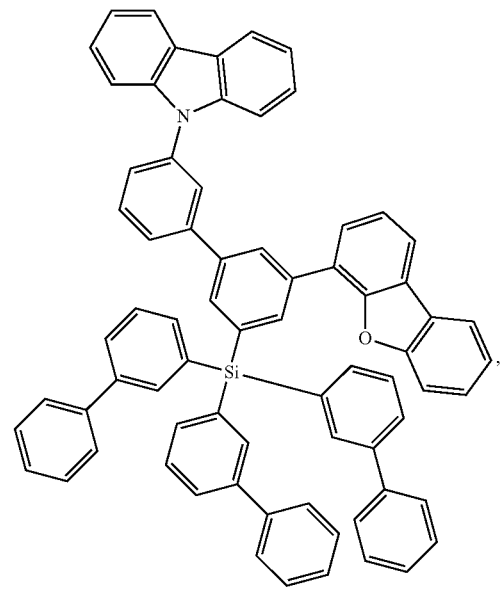
Compound 17
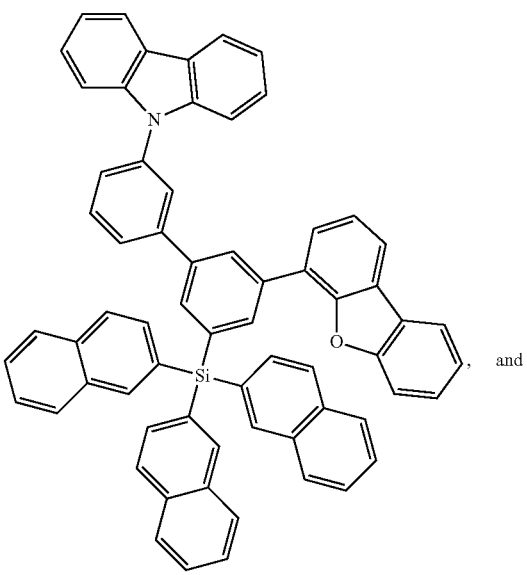
, and Compound 18

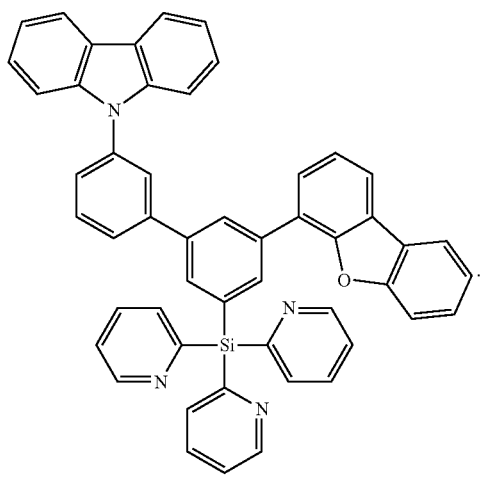

In one embodiment, a first device is provided. The first device comprises an organic light emitting device, further comprising an anode, a cathode, and an organic layer, disposed between the anode and the cathode, comprising a compound having the formula:

$L_1$-$L_2$-$L_3$    Formula I

In the compound of Formula I, $L_1$ is selected from the group consisting of carbazole, azacarbazole, triphenylene, aza-triphenylene and combinations thereof, $L_2$ is selected from the group consisting of phenyl, pyridine, pyrazine, triazine and combinations thereof, and $L_3$ is selected from the group consisting of dibenzofuran, dibenzothiophene, aza-dibenzofuran, azadibenzothiophene, dibenzoselenophene, azadibenzoselenophene, and combinations thereof. At least one of $L_1$ to $L_3$ is substituted by at least one $SiAr_1Ar_2Ar_3$ group, where $Ar_1$ to $Ar_3$ are independently selected from aryl or heteroaryl groups. Each of $L_1$ to $L_3$ is optionally substituted with a group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any optional substitution on $L_1$ and $L_3$ can be fused to $L_1$ and $L_3$ respectively, whereas any optional substitution on $L_2$ is unfused.

In one embodiment, the organic layer is an emissive layer and the compound of Formula I is a host.

In one embodiment, the first device further comprises a first dopant material that is an emissive dopant comprising a transition metal complex having at least one ligand or part of the ligand if the ligand is more than bidentate selected from the group consisting of

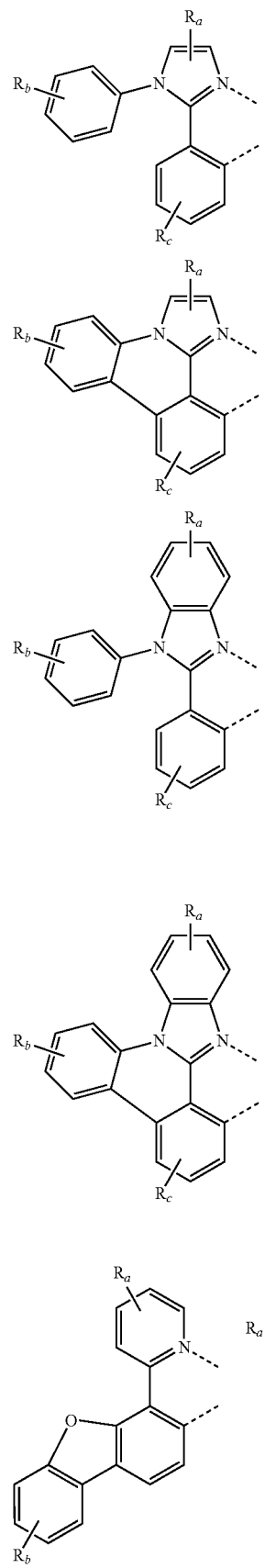

-continued

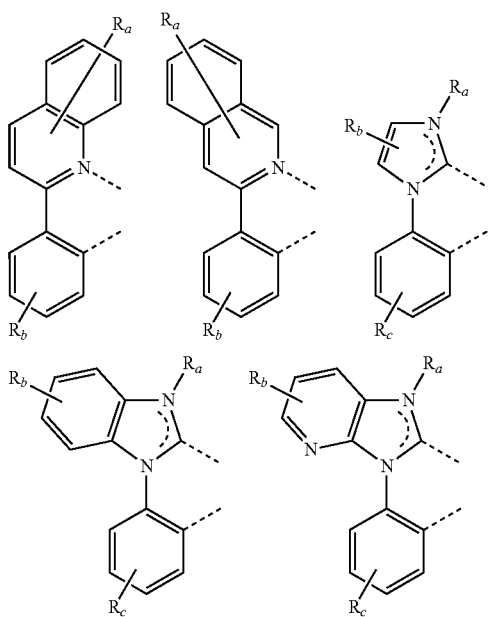

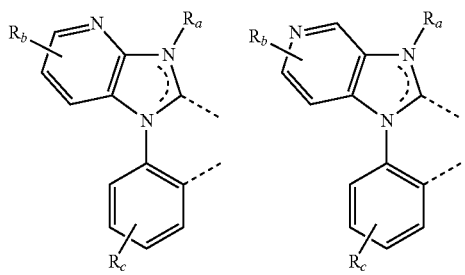

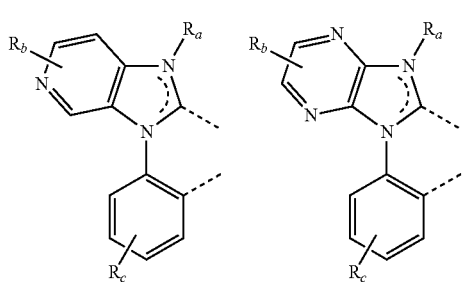

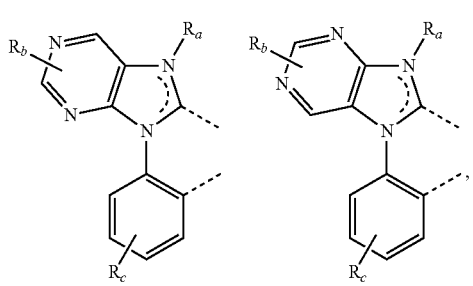

-continued

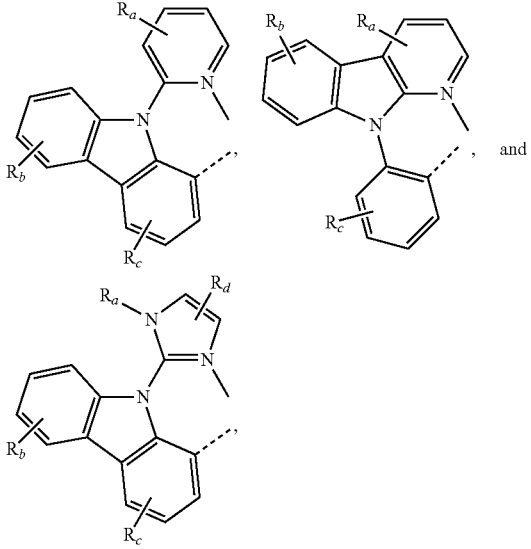

wherein $R_a$, $R_b$, $R_c$, and $R_d$ may represent mono, di, tri, or tetra substitution, or no substitution, and $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In one embodiment, the organic layer is a non-emissive layer. In one embodiment, the organic layer is a first organic layer, and the device further comprises a second organic layer that is a non-emissive layer and the compound having Formula I is a material in the second organic layer.

In one embodiment, the second organic layer is a blocking layer and the compound having Formula I is a blocking material in the second organic layer. In one embodiment, the first device is a consumer product. In one embodiment, the first device is an organic light-emitting device. In one embodiment, the first device comprises a lighting panel.

Device Examples

All example devices were fabricated by high vacuum ($<10^{-7}$ Torr) thermal evaporation (VTE). The anode electrode is 800 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the OLED device used in the Examples and Comparative Device Examples has the following structure: from the ITO surface, 100 Å of LG101 (purchased from LG Chem) as the hole injection layer, 300 Å of NPD as the hole transporting layer (HTL), 300 or 400 Å of Compounds 1, 5 or 9, or Comparative Compounds 1 or 2 doped with 20 wt % of Dopant as the emissive layer (EML), 50 Å of Compound BL as the Blocking Layer (BL) and 400 Å of Alq as the ETL. An exemplary device is depicted in the schematic in FIG. 3.

The structures of the materials used in the devices are as follows:

Dopant

Compound BL

Alq

NPD

Comparative Compound 1

Comparative Compound 2

Table 1 summarizes the performance data of phosphorescent OLED devices based on Compounds 1, 5 and 9 vs. Comparative Compounds 1 and 2. The luminous efficiency (LE), external quantum efficiency (EQE) and power efficiency (PE) were measured at 1000 nits. Compared to the device based on compounds without triarylsilane group, i.e., Comparative Compound 2, the devices based on compounds containing triarylsilane group, i.e., Compound 1 and Comparative Compound 1, exhibit improved efficiency. This could be attributed to the successful suppression of emission quenching due to the retention of high triplet energy of host materials containing triarylsilane groups (Compound 1 and Comparative Compound 1). It is noted that the efficiency of devices based on Compounds 1, 5 and 9 is further improved compared to that based on Comparative Compound 1. Although both Compounds 1, 5 and 9 and Comparative Compound 1 contain triarylsilyl group, Compounds 1, 5 and 9 have the additional feature of an asymmetric structure. By "asymmetric structure" it is meant that the groups $L_1$ and $L_3$ are different, and have different electronic properties. This asymmetric structure provides the opportunity to achieve more balanced electron/hole fluxes in OLED devices, leading to expanded recombination zone. A broader recombination zone improves device efficiency by reducing concentration quenching.

Therefore, the compounds of Formula 1 integrates the advantages of both triarylsilyl groups and asymmetric structure, and have demonstrated as superior host materials for phosphorescent OLEDs.

TABLE 1

| | | | | | | At 1000 cd/m² | | |
|---|---|---|---|---|---|---|---|---|
| Example | Host | Blocking layer | 1931 CIE x | 1931 CIE y | $\lambda_{max}$ (nm) | Voltage (V) | LE (cd/A) | EQE (%) | PE (lm/W) |
| Device Example 1 | Compound 1 | Compound BL | 0.172 | 0.384 | 474 | 5.5 | 48.2 | 21.6 | 27.3 |
| Device Example 2 | Compound 5 | Compound BL | 0.173 | 0.385 | 474 | 5.5 | 49.7 | 22.3 | 28.4 |

Comparison example EML 400A

TABLE 1-continued

| | | | Comparison example EML 400A | | | | | | |
|---|---|---|---|---|---|---|---|---|---|
| | | | | | | At 1000 cd/m² | | | |
| | | Blocking | 1931 CIE | | λ_max | Voltage | LE | EQE | PE |
| Example | Host | layer | x | y | (nm) | (V) | (cd/A) | (%) | (lm/W) |
| Device Example 3 | Compound 9 | Compound BL | 0.175 | 0.391 | 474 | 5.6 | 48.8 | 21.6 | 27.3 |
| Comparative Device Example 1 | Comparative compound 1 | Compound BL | 0.174 | 0.388 | 474 | 5.9 | 45.5 | 20.2 | 24.1 |
| Comparative Device Example 2 | Comparative compound 2 | Compound BL | 0.182 | 0.399 | 474 | 7.1 | 39.1 | 17.0 | 17.4 |

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

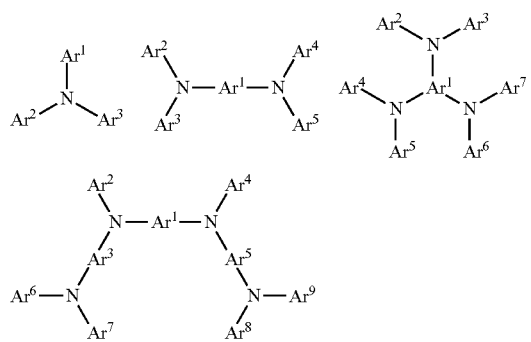

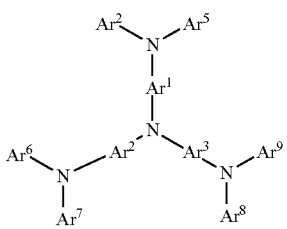

-continued

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof.

In one aspect, $Ar^1$ to $Ar^9$ is independently selected from the group consisting of:

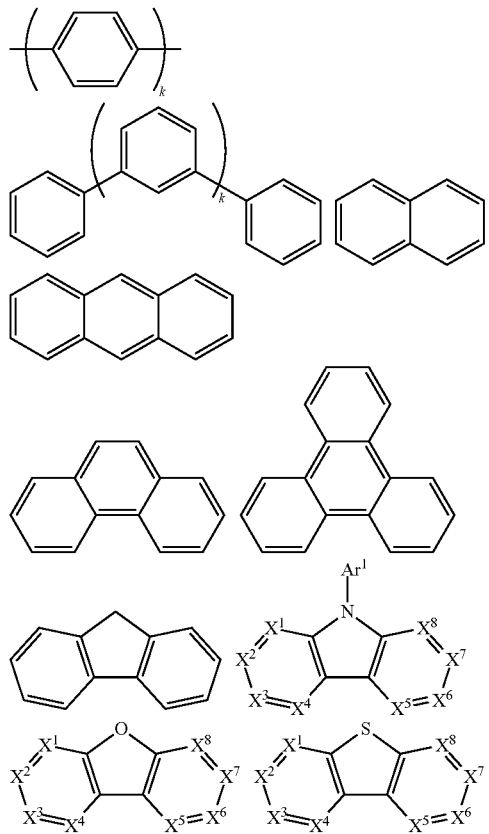

k is an integer from 1 to 20; $X^1$ to $X^8$ is C (including CH) or N; $Ar^1$ has the same group defined above.

Examples of metal complexes used in HIL or HTL include, but not limit to the following general formula:

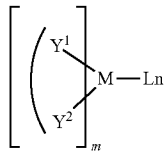

M is a metal, having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.
In another aspect, $(Y^1-Y^2)$ is a carbene ligand.
In another aspect, M is selected from Ir, Pt, Os, and Zn.
In a further aspect, the metal complex has a smallest oxidation potential in solution vs. Fc+/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

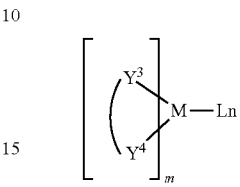

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

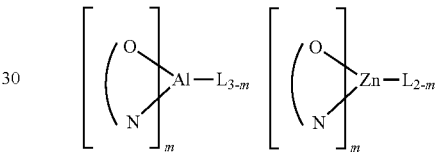

(O—N) is a bidentate ligand, having metal coordinated to atoms O and N.

In another aspect, M is selected from Ir and Pt.
In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

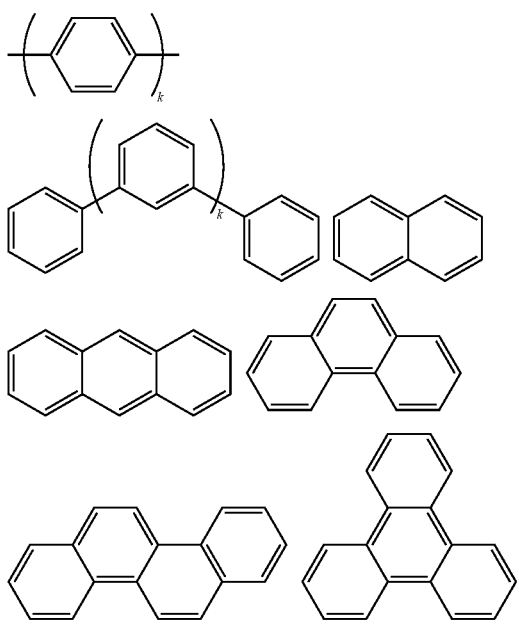

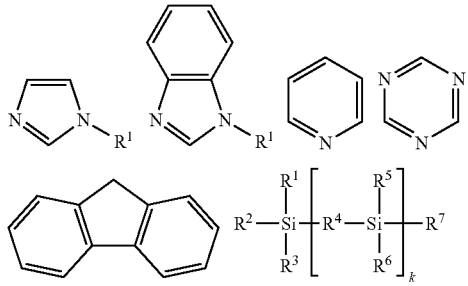

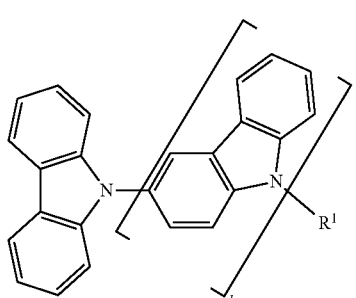

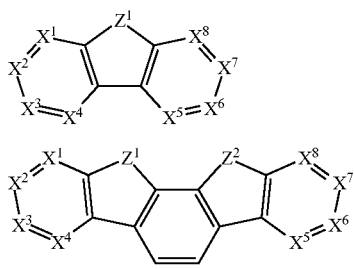

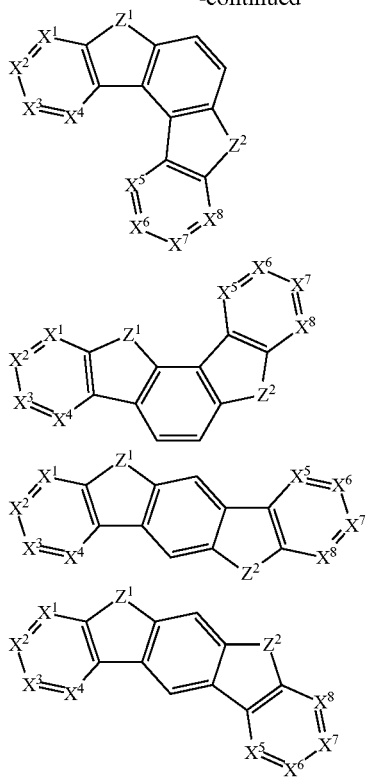

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof, when it is aryl or heteroaryl, it has the similar definition as Ar's mentioned above.

k is an integer from 0 to 20.

$X^1$ to $X^8$ is selected from C (including CH) or N.

$Z^1$ and $Z^2$ is selected from $NR^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

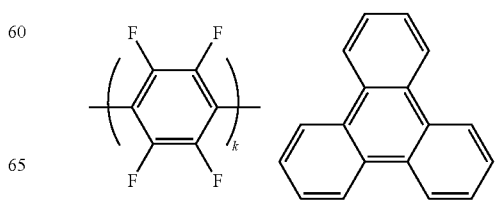

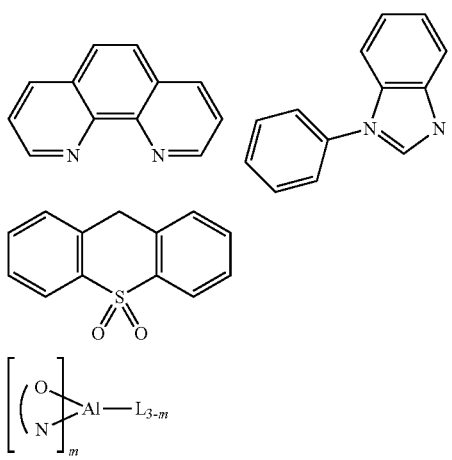

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

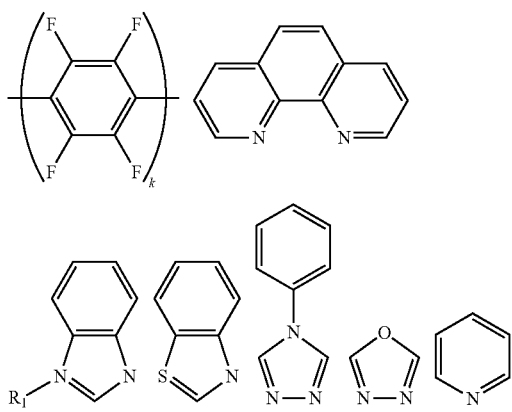

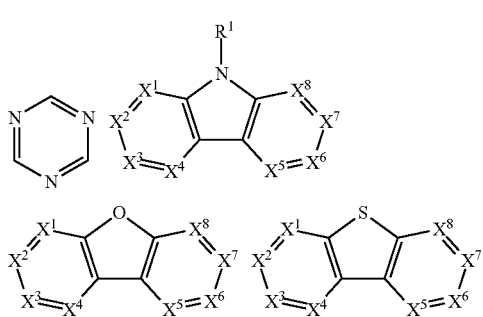

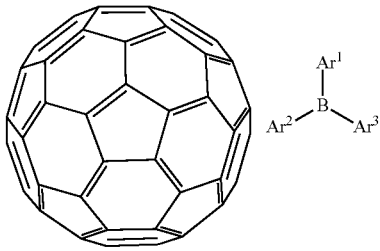

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

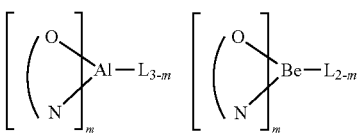

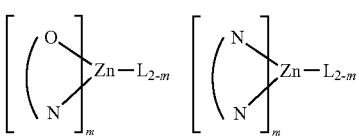

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2
| MATERIAL | EXAMPLES OF MATERIAL | PUBLICATIONS |
|---|---|---|
| Hole injection materials | | |
| Phthalocyanine and porphryin compounds | 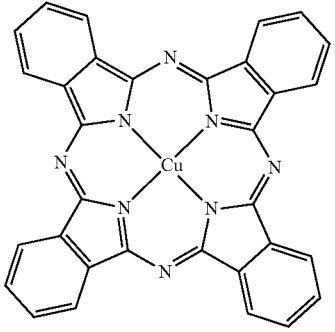 | Appl. Phys. Lett. 69, 2160 (1996) |
| Starburst triarylamines | 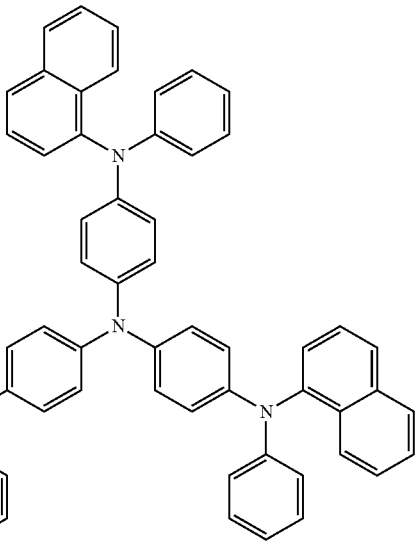 | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | 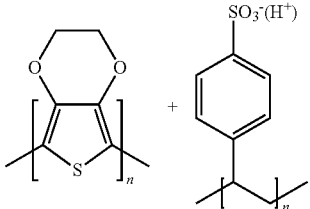 | Synth. Met. 87, 171 (1997)<br>WO2007002683 |
| Phosphonic acid and sliane SAMs | 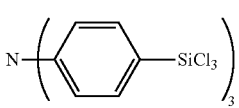 | US20030162053 |

TABLE 2-continued
| MATERIAL | EXAMPLES OF MATERIAL | PUBLICATIONS |
|---|---|---|
| Triarylamine or polythiophene polymers with conductivity dopants | 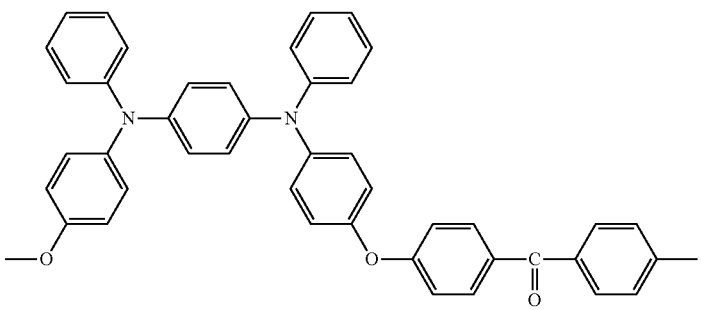 and 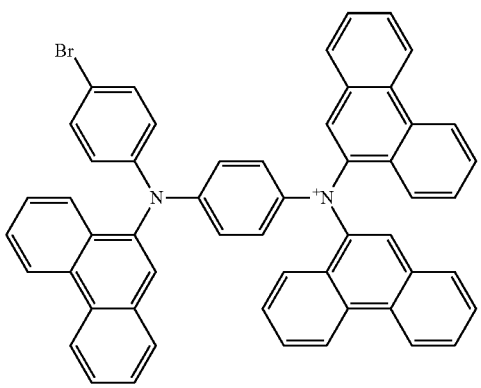 [SMILES: Brc1ccc(N(c2ccc([NH+](c3cc4ccccc4c4ccccc34)c3cc4ccccc4c4ccccc34)cc2)c2cc3ccccc3c3ccccc23)cc1]<br>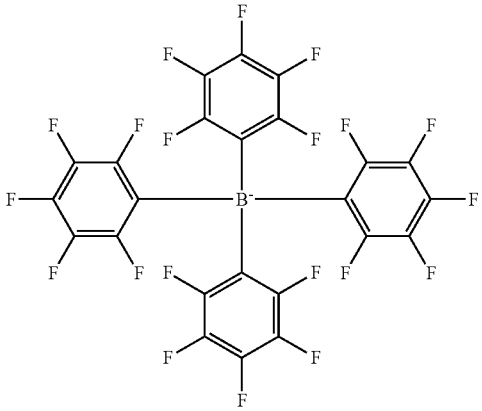 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 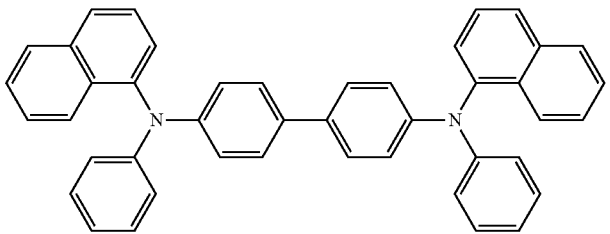 [SMILES: c1ccc(N(c2ccc(-c3ccc(N(c4ccccc4)c4cccc5ccccc45)cc3)cc2)c2cccc3ccccc23)cc1] + MoO$_x$ | US20050123751<br>SID Symposium Digest, 37, 923 (2006)<br>WO2009018009 |

TABLE 2-continued

| MATERIAL | EXAMPLES OF MATERIAL | PUBLICATIONS |
| --- | --- | --- |
| n-type semiconducting organic complexes | | US20020158242 |
| Metal organometallic complexes | | US20060240279 |
| Cross-linkable compounds | | US20080220265 |
| Polythiophene based polymers and copolymers | | WO 2011075644<br>EP2350216 |

Hole transporting materials

TABLE 2-continued

| MATERIAL | EXAMPLES OF MATERIAL | PUBLICATIONS |
|---|---|---|
| Triarylamines (e.g., TPD, α-NPD) | | Appl. Phys. Lett. 51, 913 (1987) |
| | | U.S. Pat. No. 5,061,569 |
| | | EP650955 |
| | | J. Mater. Chem. 3, 319 (1993) |

TABLE 2-continued
| MATERIAL | EXAMPLES OF MATERIAL | PUBLICATIONS |
|---|---|---|
| | 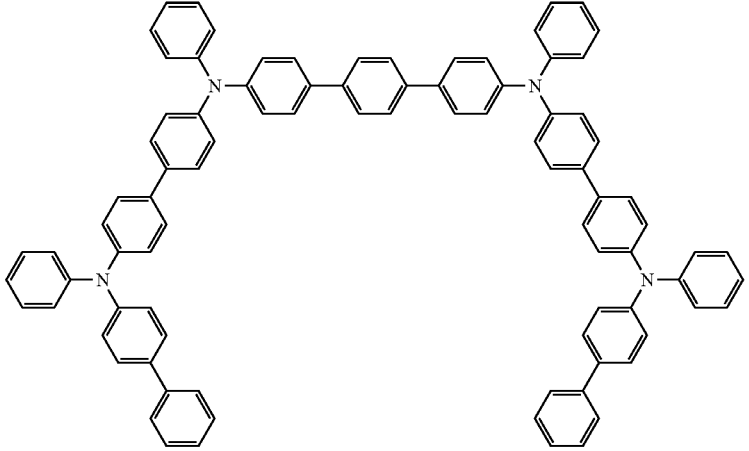 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 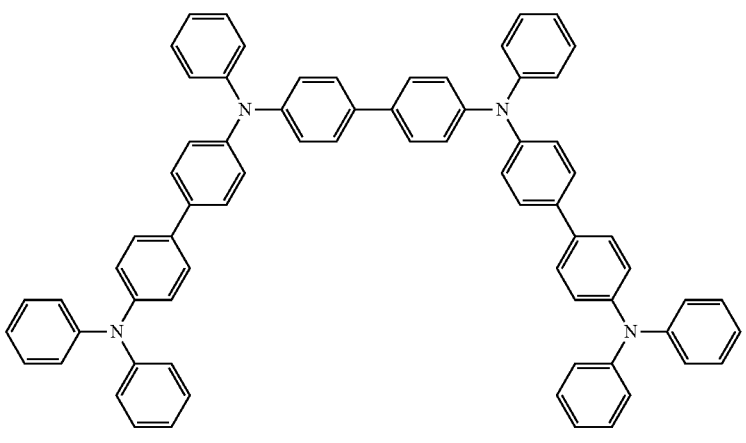 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 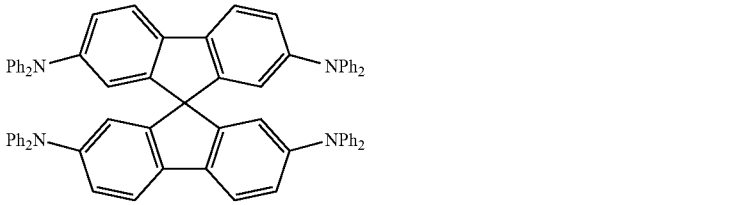 | Synth. Met. 91, 209 (1997) |
| Arylamine carbazole compounds | 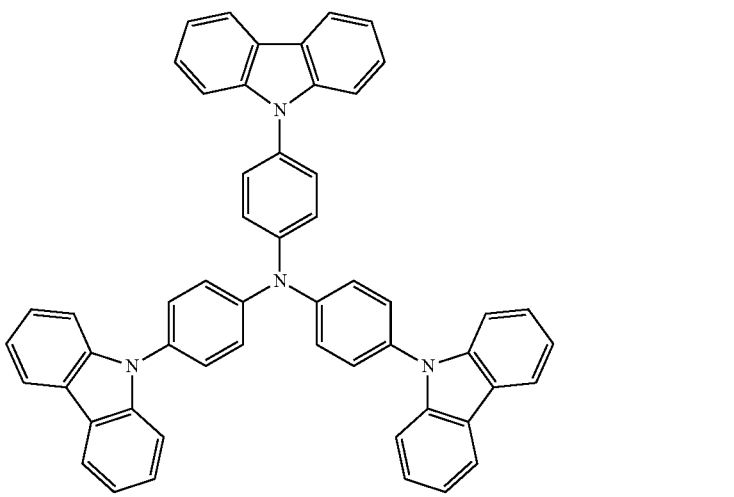 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |

TABLE 2-continued
| MATERIAL | EXAMPLES OF MATERIAL | PUBLICATIONS |
|---|---|---|
| Triarylamine with (di)benzothiophene/ (di)benzofuran | 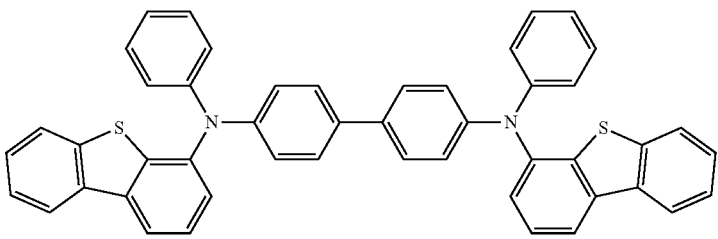 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 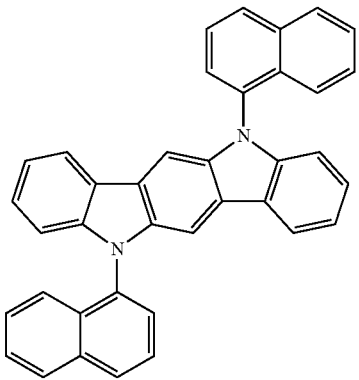 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 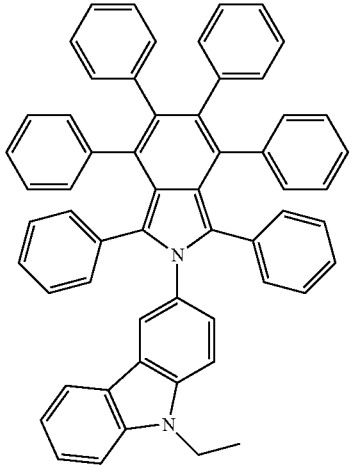 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 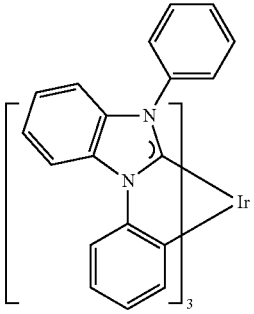 | US20080018221 |
Phosphorescent OLED host materials
Red hosts TABLE 2-continued
| MATERIAL | EXAMPLES OF MATERIAL | PUBLICATIONS |
|---|---|---|
| Arylcarbazoles | 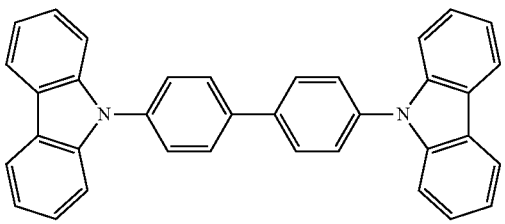 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq$_3$, BAlq) | 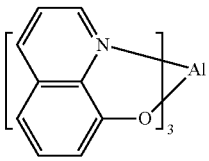 | Nature 395, 151 (1998) |
| | 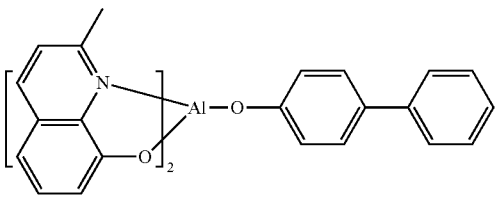 | US20060202194 |
| | 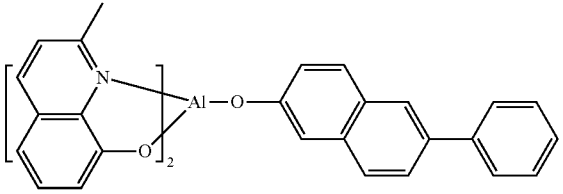 | WO2005014551 |
| | 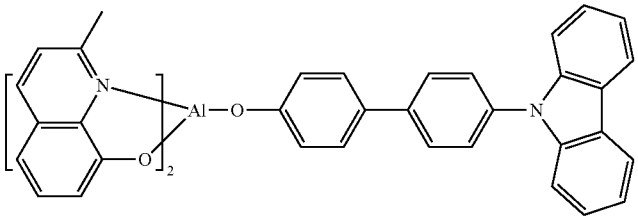 | WO2006072002 |
| Metal phenoxybenzothiazole compounds | 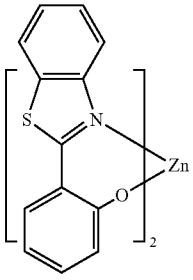 | Appl. Phys. Lett. 90, 123509 (2007) |
| Conjugated oligomers and polymers (e.g., polyfluorene) | 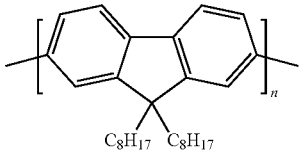 | Org. Electron. 1, 15 (2000) |

| MATERIAL | EXAMPLES OF MATERIAL | PUBLICATIONS |
|---|---|---|
| Aromatic fused rings | 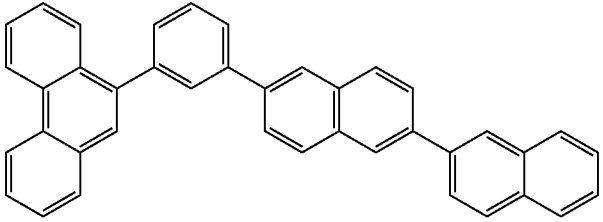 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045730, US20090045731, WO2009008311, US20090008605, US20090009065 |
| Zinc complexes | 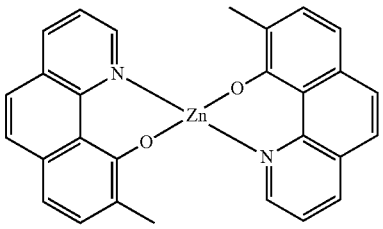 | WO2010056066 |
| Chrysene based compounds | 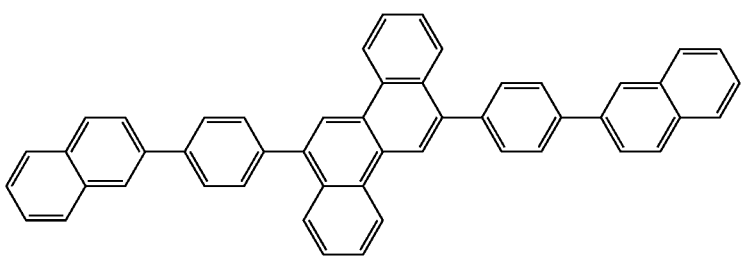 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
| Green hosts | | |
| Arylcarbazoles | 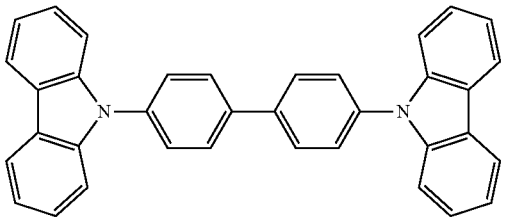 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 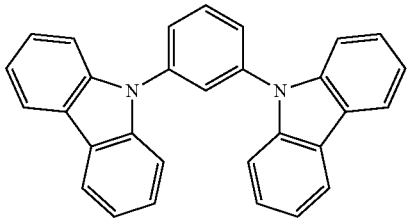 [SMILES: c1cc(-n2c3ccccc3c3ccccc32)cc(-n2c3ccccc3c3ccccc32)c1] | US20030175553 |
| | 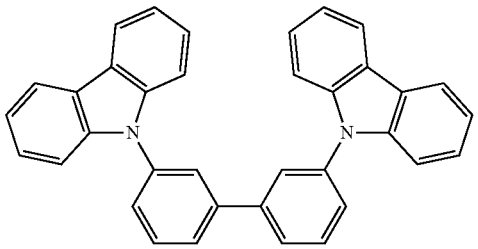 [SMILES: c1cc(-c2cccc(-n3c4ccccc4c4ccccc43)c2)cc(-n2c3ccccc3c3ccccc32)c1] | WO2001039234 |

TABLE 2-continued
| MATERIAL | EXAMPLES OF MATERIAL | PUBLICATIONS |
|---|---|---|
| Aryltriphenylene compounds | 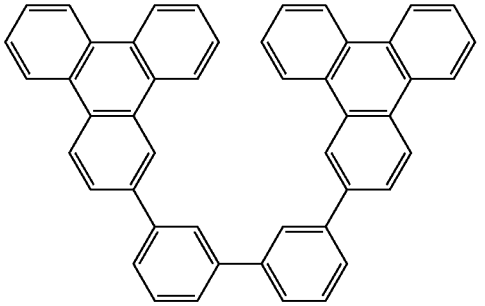 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 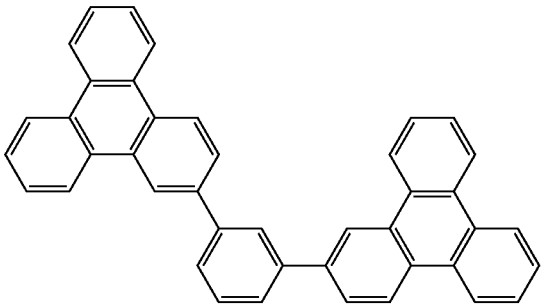 [SMILES: c1cc(-c2ccc3c4ccccc4c4ccccc4c3c2)cc(-c2ccc3c4ccccc4c4ccccc4c3c2)c1] | US20060280965 |
| | 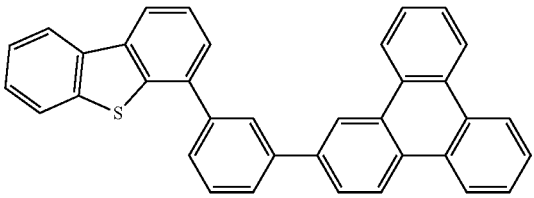 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 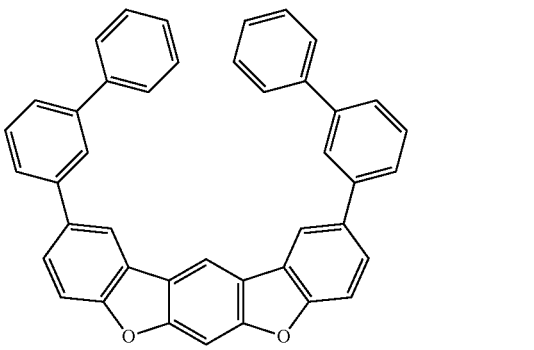 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 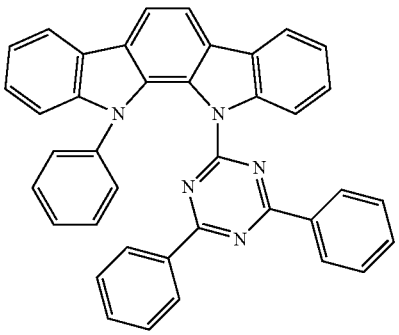 [SMILES: c1ccc(-c2nc(-c3ccccc3)nc(-n3c4ccccc4c4ccc5c6ccccc6n(-c6ccccc6)c5c43)n2)cc1] | WO2008056746 |

TABLE 2-continued

| MATERIAL | EXAMPLES OF MATERIAL | PUBLICATIONS |
|---|---|---|
| | | WO2010107244 |
| Aza-carbazole/DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |

TABLE 2-continued
| MATERIAL | EXAMPLES OF MATERIAL | PUBLICATIONS |
|---|---|---|
| Metal phenoxybenzooxazole compounds | 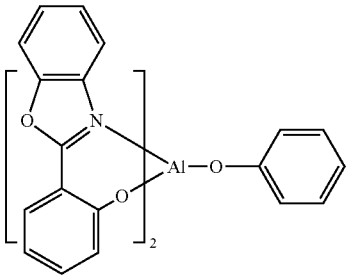 | WO2005089025 |
|  | 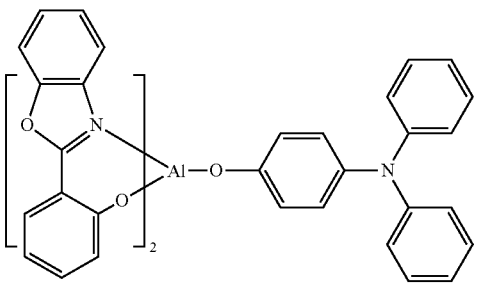 | WO2006132173 |
|  | 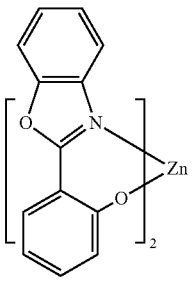 | JP200511610 |
| Spirofluorene-carbazole compounds | 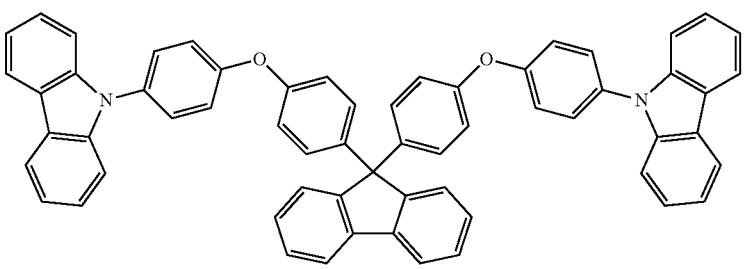 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
|  | 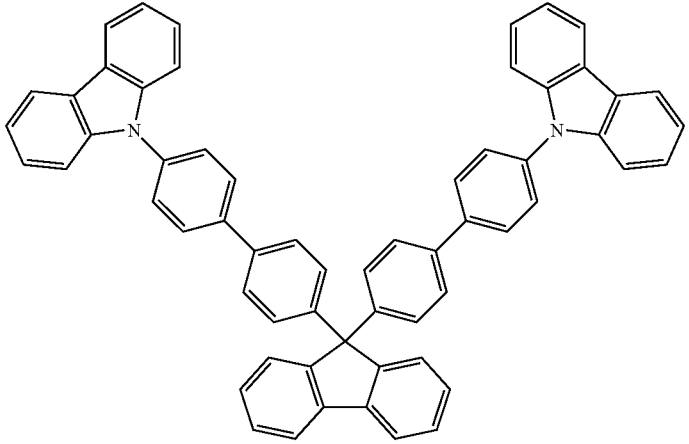 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |

TABLE 2-continued

| MATERIAL | EXAMPLES OF MATERIAL | PUBLICATIONS |
|---|---|---|
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 2-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |

Blue hosts

| | | |
| --- | --- | --- |
| Arylcarbazoles | | Appl. Phys. Lett. 82, 2422 (2003) |
| | | US20070190359 |
| Dibenzothiophene/ Dibenzofuran-carbazole compounds | | WO2006114966, US20090167162 |
| | | US20090167162 |

TABLE 2-continued
| MATERIAL | EXAMPLES OF MATERIAL | PUBLICATIONS |
|---|---|---|
| | 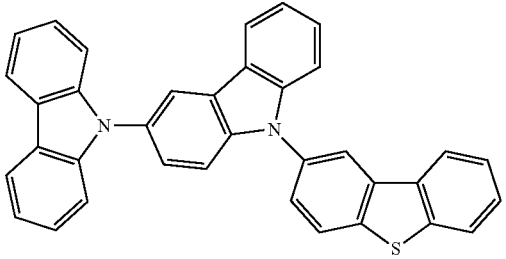 [SMILES: c1ccc2c(c1)sc1ccc(-n3c4ccccc4c4cc(-n5c6ccccc6c6ccccc65)ccc43)cc12] | WO2009086028 |
| | 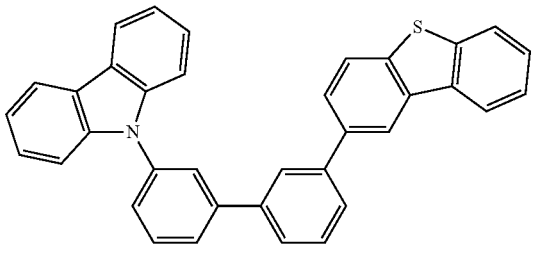 [SMILES: c1cc(-c2cccc(-n3c4ccccc4c4ccccc43)c2)cc(-c2ccc3sc4ccccc4c3c2)c1] | US20090030202, US20090017330 |
| | 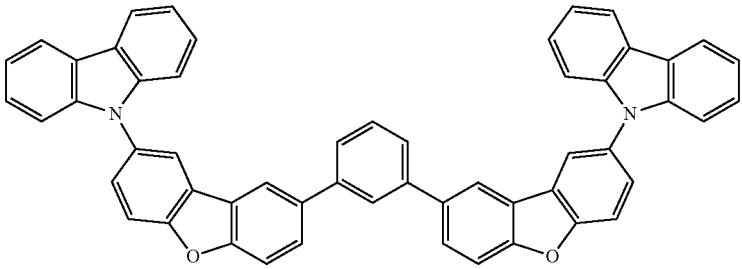 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 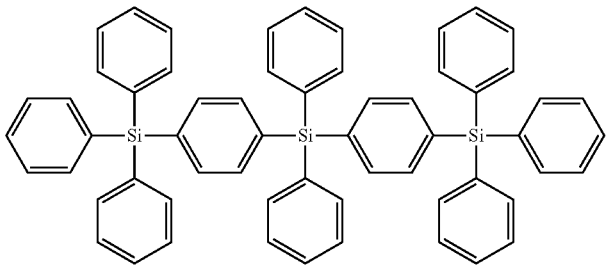 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 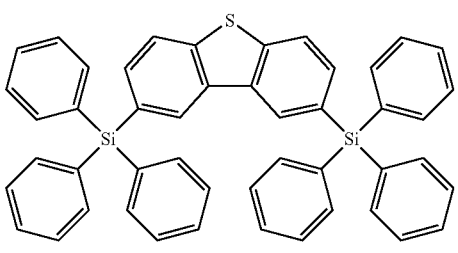 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 2-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

Phosphorescent dopants

Red dopants

TABLE 2-continued

| MATERIAL | EXAMPLES OF MATERIAL | PUBLICATIONS |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

TABLE 2-continued

| MATERIAL | EXAMPLES OF MATERIAL | PUBLICATIONS |
| --- | --- | --- |
| | | US20060202194 |
| | | US20070087321 |
| | | US20080261076<br>US20100090591 |
| | | US20070087321 |
| | | Adv. Mater. 19, 739 (2007) |

TABLE 2-continued

| MATERIAL | EXAMPLES OF MATERIAL | PUBLICATIONS |
| --- | --- | --- |
|  |  | WO2009100991 |
|  |  | WO2008101842 |
|  |  | U.S. Pat. No. 7,232,618 |
| Platinum(II) organometallic complexes |  | WO2003040257 |
|  |  | US20070103060 |

TABLE 2-continued

| MATERIAL | EXAMPLES OF MATERIAL | PUBLICATIONS |
| --- | --- | --- |
| Osminum(III) complexes | [structure: F$_3$C-pyrazole-pyridine]$_2$Os(PPhMe$_2$)$_2$ | Chem. Mater. 17, 3532 (2005) |
| Ruthenium(II) complexes | [structure: $^t$Bu-pyrazole-isoquinoline]$_2$Ru(PPhMe$_2$)$_2$ | Adv. Mater. 17, 1059 (2005) |
| Rhenium (I), (II), and (III) complexes | [structure: 8-hydroxyquinoline-Re-(CO)$_4$] | US20050244673 |

Green dopants

| | | |
| --- | --- | --- |
| Iridium(III) organometallic complexes | [structure: Ir(ppy)$_3$] and its derivatives | Inorg. Chem. 40, 1704 (2001) |
| | [structure: Ir(ppy)$_2$(acac)] | US20020034656 |

TABLE 2-continued

| MATERIAL | EXAMPLES OF MATERIAL | PUBLICATIONS |
|---|---|---|
| | | U.S. Pat. No. 7,332,232 |
| | | US20090108737 |
| | | WO2010028151 |

TABLE 2-continued

| MATERIAL | EXAMPLES OF MATERIAL | PUBLICATIONS |
|---|---|---|
| | | EP1841834B |
| | | US20060127696 |
| | | US20090039776 |
| | | U.S. Pat. No. 6,921,915 |
| | | US20100244004 |

TABLE 2-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US 20060008670<br>JP2007123392 |
| | | WO2010086089,<br>WO2011044988 |
| | | Adv. Mater. 16, 2003 (2004) |

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| | | US20010015432 |

| MATERIAL | EXAMPLES OF MATERIAL | PUBLICATIONS |
|---|---|---|
| | | US20100295032 |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |

TABLE 2-continued
| MATERIAL | EXAMPLES OF MATERIAL | PUBLICATIONS |
|---|---|---|
| | 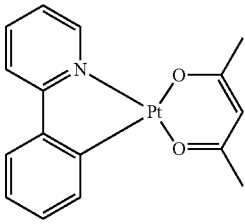 | WO2002015645 |
| | 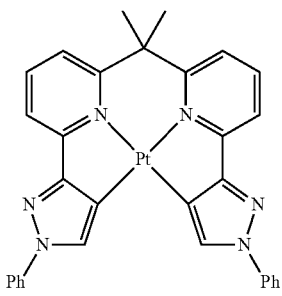 | US20060263635 |
| | 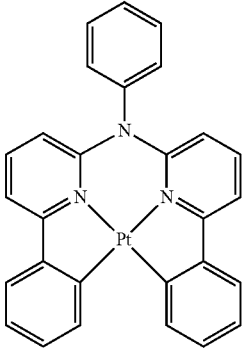 | US20060182992<br>US20070103060 |
| Cu complexes | 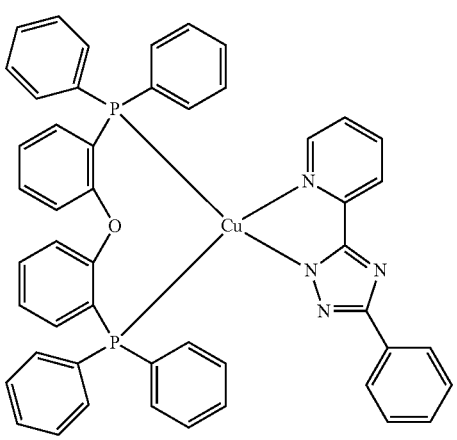 | WO2009000673 |

TABLE 2-continued

| MATERIAL | EXAMPLES OF MATERIAL | PUBLICATIONS |
|---|---|---|
| | | US20070111026 |
| Gold complexes | | Chem. Commun. 2906 (2005) |
| Rhenium(III) complexes | | Inorg. Chem. 42, 1248 (2003) |
| Osmium(II) complexes | | U.S. Pat. No. 7,279,704 |

TABLE 2-continued

| MATERIAL | EXAMPLES OF MATERIAL | PUBLICATIONS |
| --- | --- | --- |
| Deuterated organometallic complexes | | US20030138657 |
| Organometallic complexes with two or more metal centers | | US20030152802 |
| | | U.S. Pat. No. 7,090,928 |

Blue dopants

| | | |
| --- | --- | --- |
| Iridium(III) organometallic complexes | | WO2002002714 |

TABLE 2-continued
| MATERIAL | EXAMPLES OF MATERIAL | PUBLICATIONS |
|---|---|---|
| | 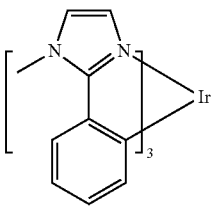 | WO2006009024 |
| | 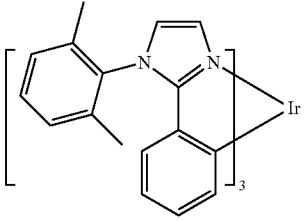 | US20060251923<br>US20110057559<br>US20110204333 |
| | 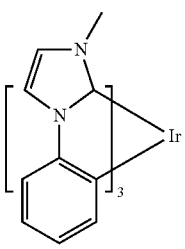 | U.S. Pat. No. 7,393,599,<br>WO2006056418,<br>US20050260441,<br>WO2005019373 |
| | 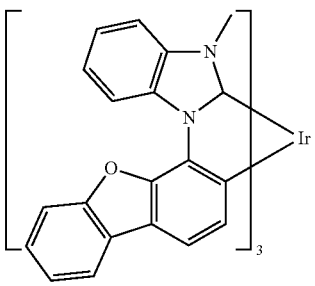 | U.S. Pat. No. 7,534,505 |
| | 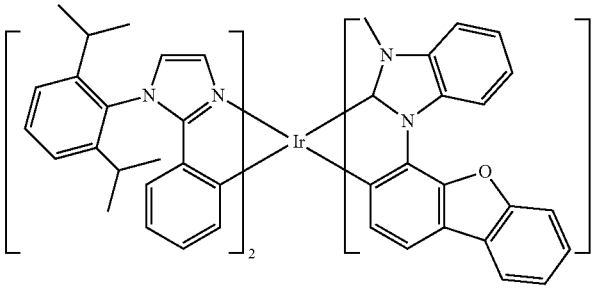 | WO2011051404 |
| | 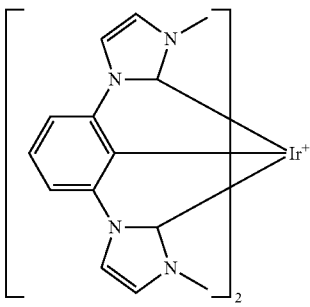 | U.S. Pat. No. 7,445,855 |

TABLE 2-continued

| MATERIAL | EXAMPLES OF MATERIAL | PUBLICATIONS |
|---|---|---|
| | | US20070190359, US20080297033 US20100148663 |
| | | U.S. Pat. No. 7,338,722 |
| | | US20020134984 |
| | | Angew. Chem. Int. Ed. 47, 1 (2008) |
| | | Chem. Mater. 18, 5119 (2006) |

TABLE 2-continued

| MATERIAL | EXAMPLES OF MATERIAL | PUBLICATIONS |
|---|---|---|
| | | Inorg. Chem. 46, 4308 (2007) |
| | | WO2005123873 |
| | | WO2005123873 |
| | | WO2007004380 |
| | | WO2006082742 |

TABLE 2-continued
| MATERIAL | EXAMPLES OF MATERIAL | PUBLICATIONS |
|---|---|---|
| Osmium(II) complexes | 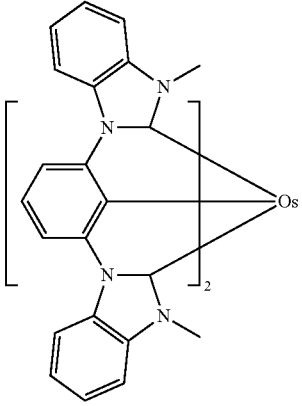 | U.S. Pat. No. 7,279,704 |
| | 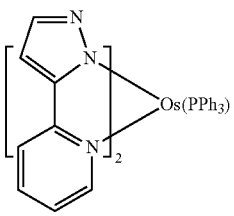 | Organometallics 23, 3745 (2004) |
| Gold complexes | 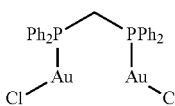 | Appl. Phys. Lett. 74, 1361 (1999) |
| Platinum(II) complexes | 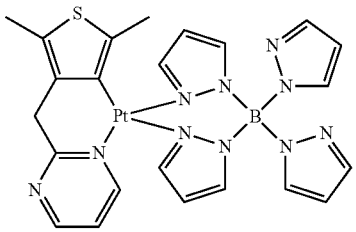 | WO2006098120, WO2006103874 |
| Pt tetradentate complexes with at least one metal-carbene bond | 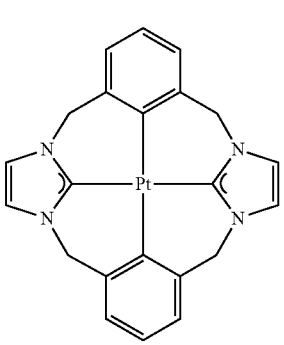 | U.S. Pat. No. 7,655,323 |
| Exciton/hole blocking layer materials | | |
| Bathocuprine compounds (e.g., BCP, BPhen) | 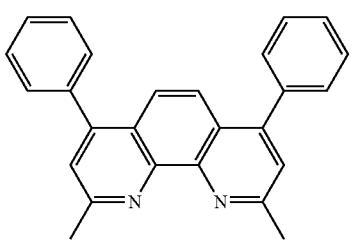 [SMILES: Cc1cc(-c2ccccc2)c2ccc3c(-c4ccccc4)cc(C)nc3c2n1] | Appl. Phys. Lett. 75, 4 (1999) |

TABLE 2-continued

| MATERIAL | EXAMPLES OF MATERIAL | PUBLICATIONS |
| --- | --- | --- |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |
| Triphenylene compounds | | US20050025993 |

TABLE 2-continued

| MATERIAL | EXAMPLES OF MATERIAL | PUBLICATIONS |
|---|---|---|
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |

Electron transporting materials

TABLE 2-continued

| MATERIAL | EXAMPLES OF MATERIAL | PUBLICATIONS |
|---|---|---|
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987)<br>U.S. Pat. No. 7,230,107 |

TABLE 2-continued
| MATERIAL | EXAMPLES OF MATERIAL | PUBLICATIONS |
| --- | --- | --- |
| Metal hydroxybenoquinolates | 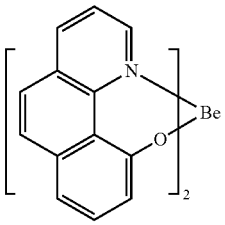 | Chem. Lett. 5, 905 (1993) |
| Bathocuprine compounds such as BCP, BPhen, etc | 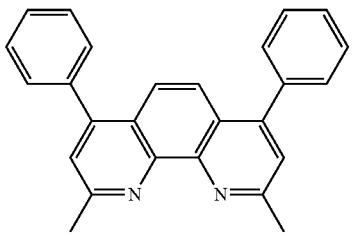 [SMILES: Cc1cc(-c2ccccc2)c2ccc3c(-c4ccccc4)cc(C)nc3c2n1] | Appl. Phys. Lett. 91, 263503 (2007) |
|  | 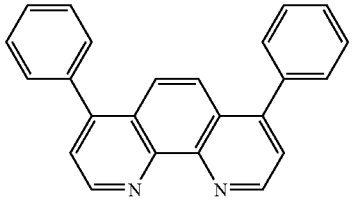 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 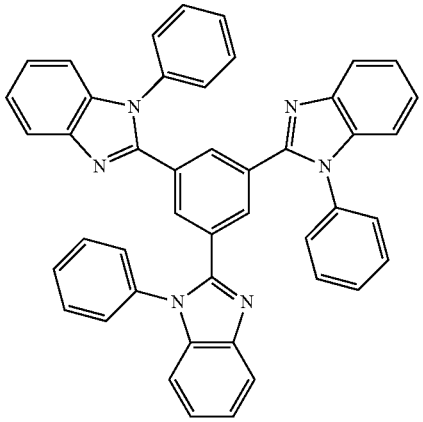 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
|  | 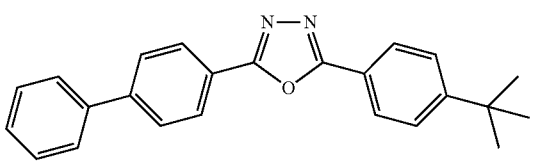 [SMILES: CC(C)(C)c1ccc(-c2nnc(-c3ccc(-c4ccccc4)cc3)o2)cc1] | Appl. Phys. Lett. 55, 1489 (1989) |
|  | 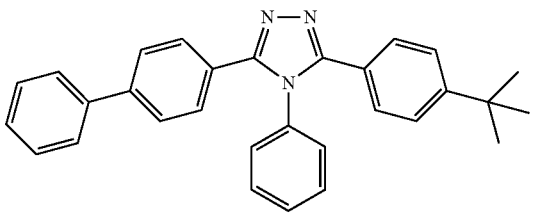 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |

TABLE 2-continued
| MATERIAL | EXAMPLES OF MATERIAL | PUBLICATIONS |
| --- | --- | --- |
| Silole compounds | 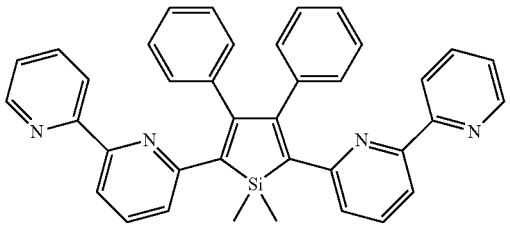 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 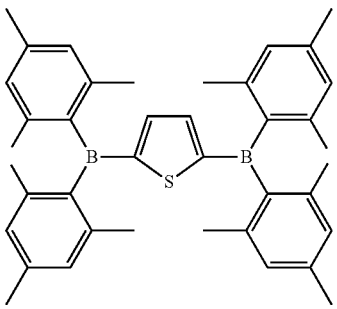 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |
| Fluorinated aromatic compounds | 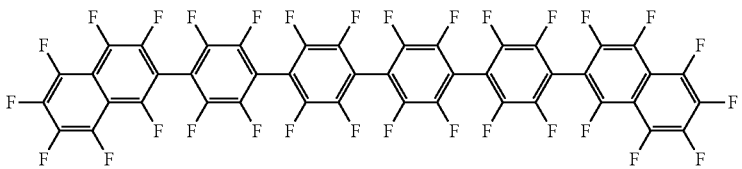 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 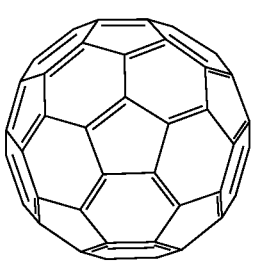 | US20090101870 |
| Triazine complexes | 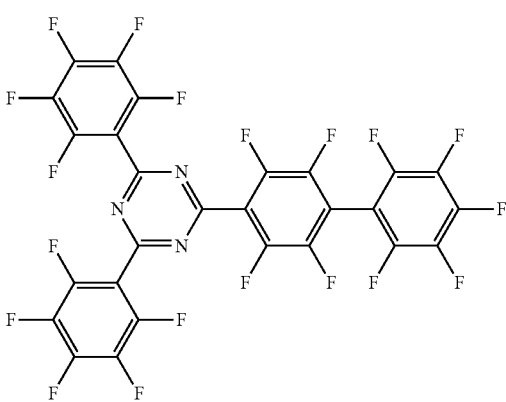 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

| MATERIAL | EXAMPLES OF MATERIAL | PUBLICATIONS |
|---|---|---|
| Zn (N^N) complexes | 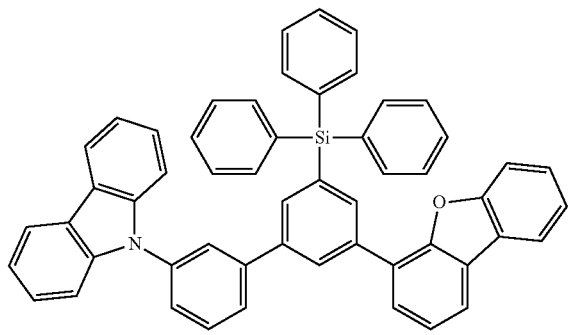 | U.S. Pat. No. 6,528,187 |

EXPERIMENTAL

Chemical abbreviations used throughout this document are as follows: dba is dibenzylideneacetone, EtOAc is ethyl acetate, PPh₃ is triphenylphosphine, dppf is 1,1'-bis(diphenylphosphino)ferrocene, DCM is dichloromethane, SPhos is dicyclohexyl(2',6'-dimethoxy-[1,1'-biphenyl]-3-yl)phosphine, THE is tetrahydrofuran.

Synthesis of Compounds

Compound 1

Compound 1

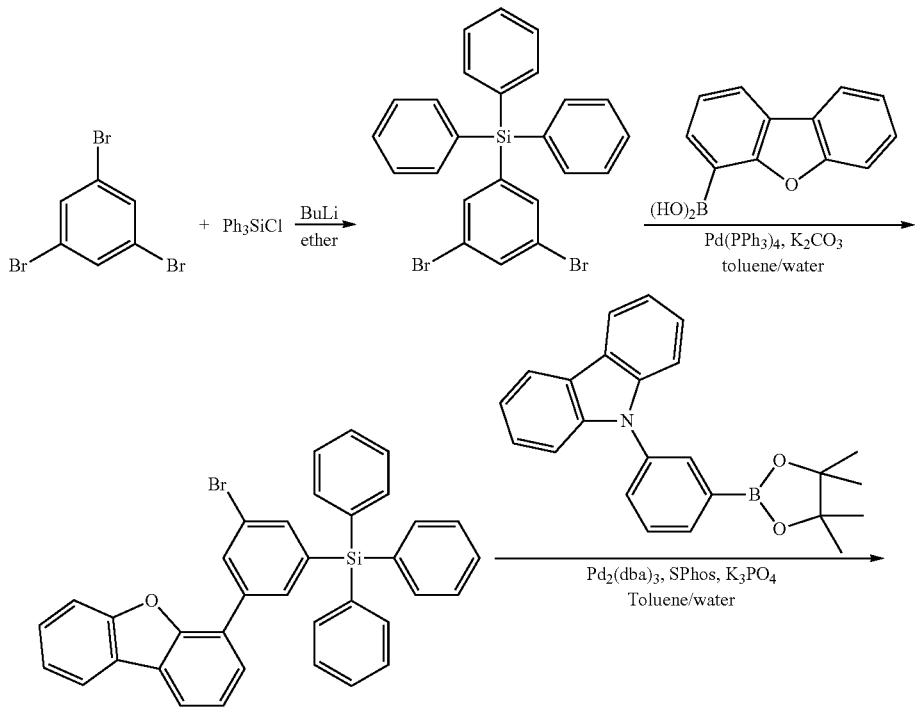

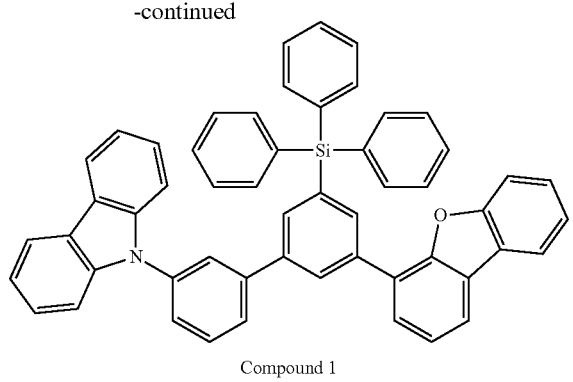

Compound 1

Synthesis of (3,5-dibromophenyl)triphenylsilane

Into a solution of 1,3,5-tribromobenzene (9.0 g, 28.6 mmol) in diethyl ether (200 mL) was added n-butyllithium solution in hexane (2.5 M, 12 mL, 30.6 mmol) dropwise at −78° C. The reaction was stirred at this temperature for 30 minutes before a solution of chlorotriphenylsilane (9.27 g, 31.4 mmol) in diethyl ether (90 mL) was added dropwise. The reaction mixture was stirred at −78° C. for 1 hour, and then allowed to warm to room temperature and continue to stir overnight, and finally refluxed for 2 hours. After cooling to room temperature, the solid was filtered off. Upon evaporation of the solvent, the residue was purified by column chromatography on silica gel with hexane/DCM (9/1, v/v) as eluent to yield (3,5-dibromophenyl)triphenylsilane (4.0 g, 28%) as a white solid.

Synthesis of (3-bromo-5-(dibenzo[b,d]furan-4-yl)phenyl)triphenylsilane

A solution of (3,5-dibromophenyl)triphenylsilane (4.66 g, 9.43 mmol), dibenzo[b,d]furan-4-ylboronic acid (1.00 g, 4.72 mmol), Pd(PPh$_3$)$_4$ (0.109 g, 0.094 mmol) and potassium carbonate (1.304 g, 9.43 mmol) in toluene (150 mL) and water (25 mL) was refluxed under nitrogen overnight. The organic phase was isolated, filtered and evaporated. The residue was purified by column chromatography on silica gel with hexane/DCM (4/1, v/v) as eluent to yield (3-bromo-5-(dibenzo[b,d]furan-4-yl)phenyl)triphenylsilane (1.75 g, 64% yield) as a white solid.

Synthesis of Compound 1

A solution of (3-Bromo-5-(dibenzo[b,d]furan-4-yl)phenyl)triphenylsilane (3.00 g, 5.16 mmol), 9-(3-(4,4,5,5-tetramethyl-1,3,2-dioxaborolan-2-yl)phenyl)-91'-carbazole (1.905 g, 5.16 mmol), Pd$_2$(dba)$_3$ (0.094 g, 0.103 mmol), SPhos (0.085 g, 0.206 mmol) and K$_3$PO$_4$ (3.56 g, 15.48 mmol) in toluene (100 mL) and water (5 mL), was refluxed under nitrogen overnight. After cooling to room temperature, the solid was filtered off. Upon evaporation of the solvent, the residue was purified by column chromatography on silica gel with hexane/DCM (4/1, v/v) as eluent, followed by column chromatography on alumina with hexane/DCM (3/1, v/v) as eluent to yield Compound 1 (1.5 g, 39% yield) as a white solid.

Compound 2

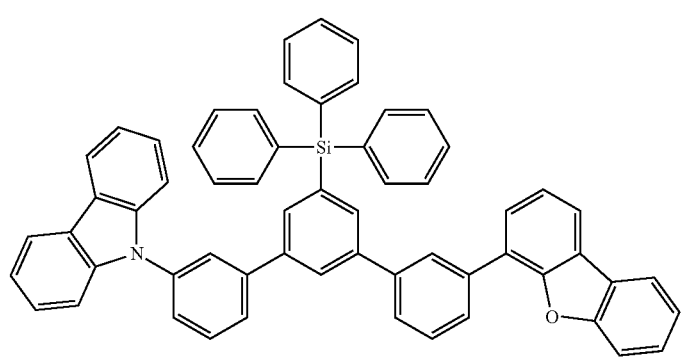

Compound 2

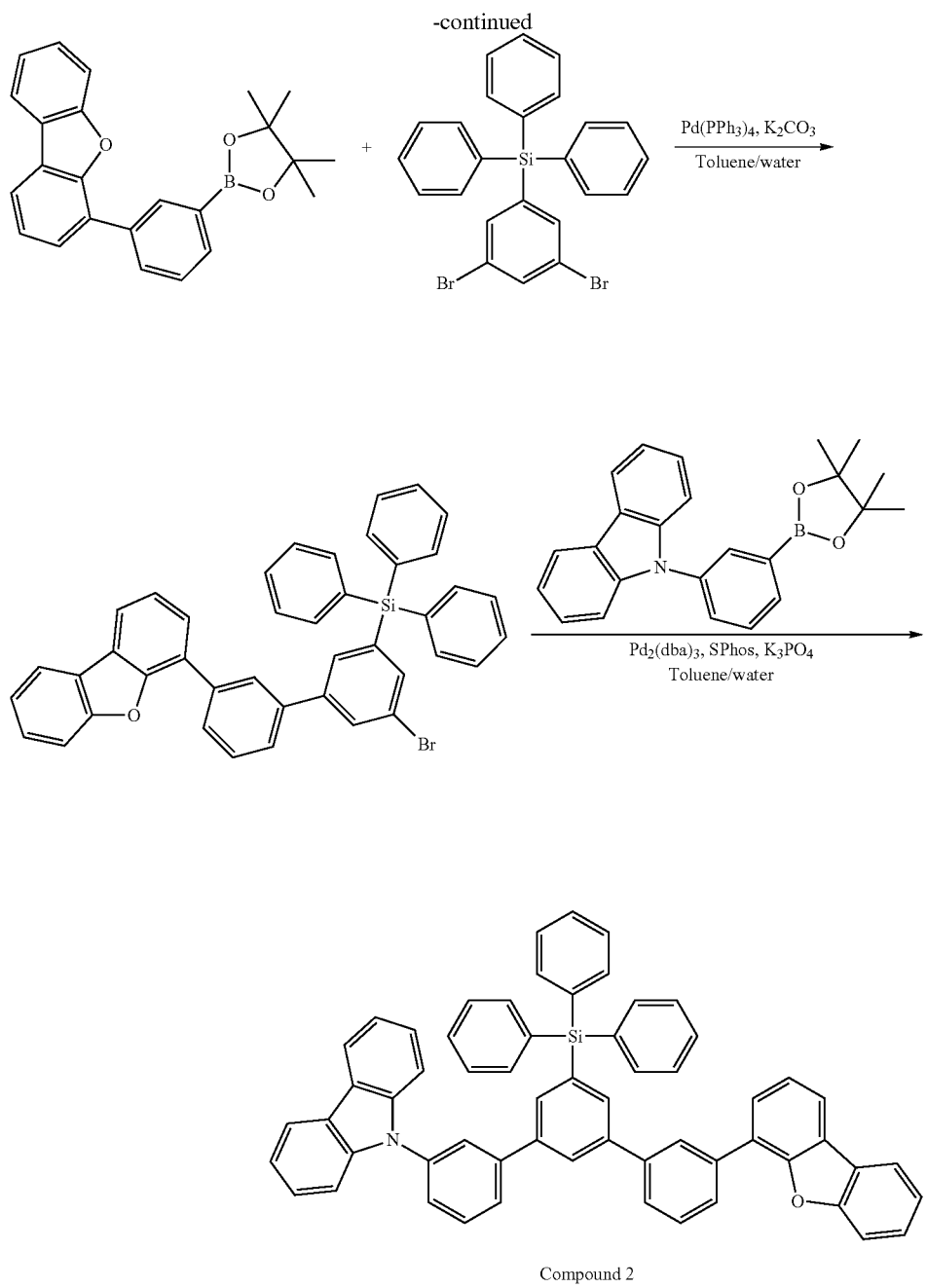

Synthesis of (5-bromo-3'-(dibenzo[b,d]furan-4-yl)-[1,1'-biphenyl]-3-yl)triphenylsilane A solution of (3,5-Dibromophenyl)triphenylsilane (4.27 g, 8.64 mmol), 2-(3-(dibenzo[b,d]furan-4-yl)phenyl)-4,4,5,5-tetramethyl-1,3,2-dioxaborolane (1.6 g, 4.32 mmol), Pd(PPh$_3$)$_4$ (0.100 g, 0.086 mmol) and K$_2$CO$_3$ (1.792 g, 12.96 mmol) in toluene (100 mL) and water (10 mL) was refluxed under nitrogen overnight. After cooling to room temperature, the organic phase was isolated, and the solvent was evaporated. The residue was purified by column chromatography on silica gel with hexane/DCM (4/1 to 3/1, v/v) as eluent to yield (5-Bromo-3'-(dibenzo[b,d]furan-4-yl)[1,1'-biphenyl]-3-yl)triphenylsilane (1.3 g, 45%) as a white solid.

Synthesis of Compound 2

A solution of (5-bromo-3'-(dibenzo[b,d]furan-4-yl)[1,1'-biphenyl]-3-yl)triphenylsilane (2.17 g, 3.31 mmol), 9-(3-(4,4,5,5-tetramethyl-1,3,2-dioxaborolan-2-yl)phenyl)-9H-carbazole (1.35 g, 3.65 mmol), Pd$_2$(dba)$_3$ (0.061 g, 0.066 mmol), SPhos (0.054 g, 0.132 mmol) and K$_3$PO$_4$ (2.11 g, 9.94 mmol) in toluene (100 mL) and water (2 mL) was refluxed under nitrogen overnight. After cooling to room temperature, the organic phase was isolated and the solvent was evaporated. The residue was purified by column chromatography on silica gel with hexane/DCM (3/1, v/v) as eluent to yield Compound 2 (2.4 g, 88%) as a white solid.

Compound 5

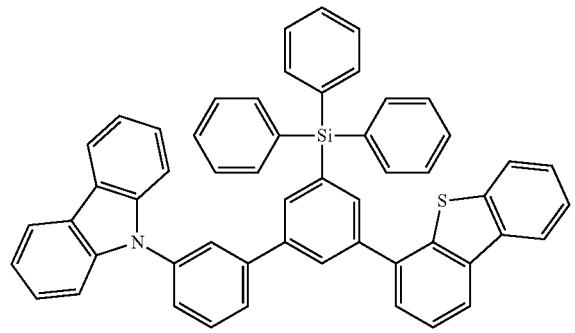

Compound 5

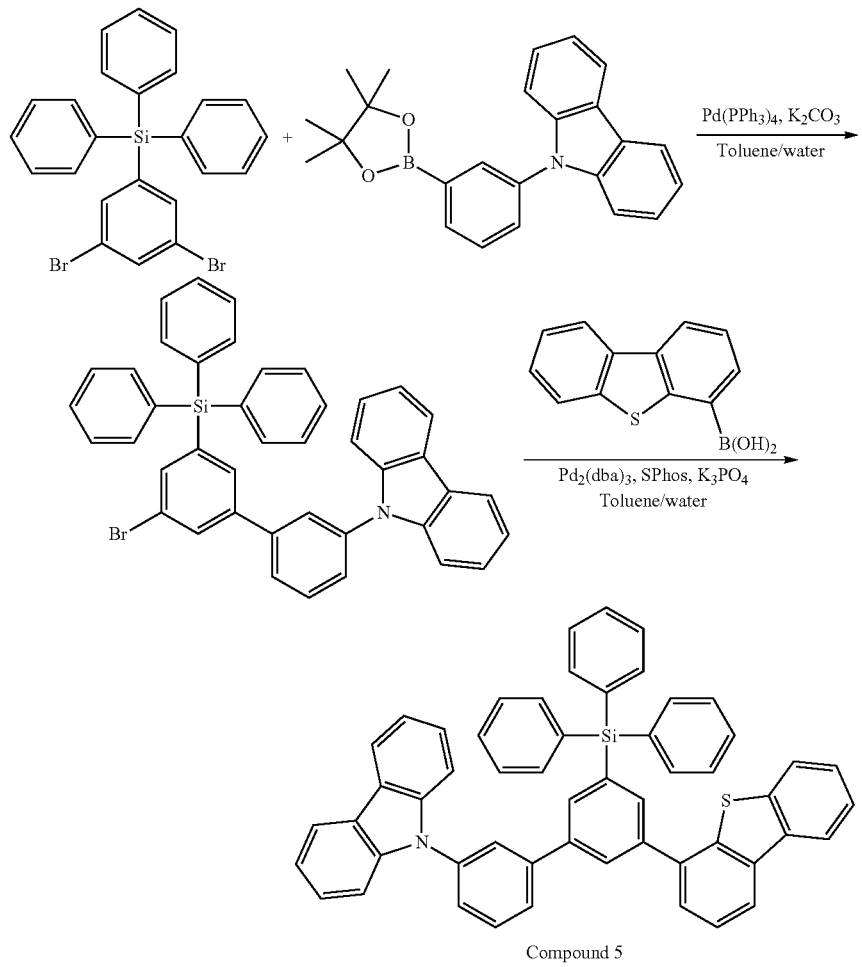

Compound 5

Synthesis of 9-(3'-Bromo-5'-(triphenylsilyl)-[1,1'-biphenyl]-3-yl)-9H-carbazole

A solution of (3,5-dibromophenyl)triphenylsilane (4.02 g, 8.12 mmol), 9-(3-(4,4,5,5-tetramethyl-1,3,2-dioxaborolan-2-yl)phenyl)-9H-carbazole (1.500 g, 4.06 mmol), Pd(PPh$_3$)$_4$ (100 mg, 0.086 mmol), K$_2$CO$_3$ (1.123 g, 8.12 mmol) in toluene (100 mL) and water (20 mL) was refluxed under nitrogen for 24 h. After cooling to room temperature, the organic phase was isolated and the solvent was evaporated. The residue was purified by column chromatography on silica gel with hexane/DCM (9/1 to 4/1, v/v) as eluent and recrystallized from hexane/DCM (9/1, v/v) to yield 9-(3'-Bromo-5'-(triphenylsilyl)-[1,1'-biphenyl]-3-yl)-9H-carbazole (2.1 g, 79%) as white crystals.

Synthesis of Compound 5

A solution of 9-(3'-Bromo-5'-(triphenylsilyl)-[1,1'-biphenyl]-3-yl)-9H-carbazole (2.97 g, 4.52 mmol) and dibenzo[b,d]thiophen-4-ylboronic acid (1.032 g, 4.52 mmol), Pd$_2$(dba)$_3$ (0.20 g, 0.021 mmol), SPhos (0.20 g, 0.049 mmol) and K$_3$PO$_4$ (2.88 g, 13.57 mmol) in toluene (120 mL) and water (5 mL) was refluxed under nitrogen overnight. After cooling to room temperature, the organic phase was isolated and the solvent was evaporated. The residue was purified by column chromatography on silica gel with hexane/DCM (4/1, v/v) as eluent to provide Compound 5 (2.5 g, 72.5%) as a white solid.

Compound 8

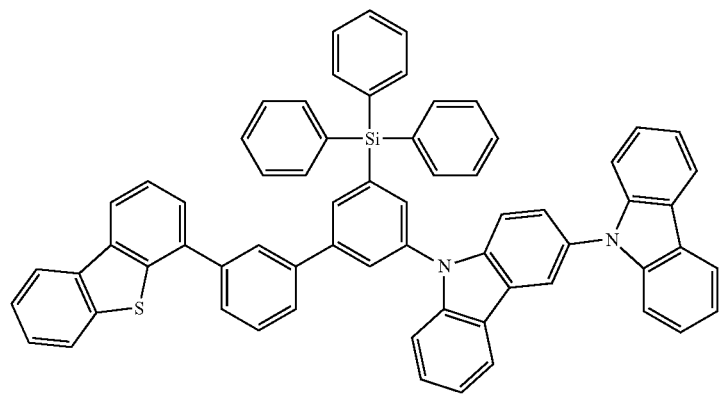

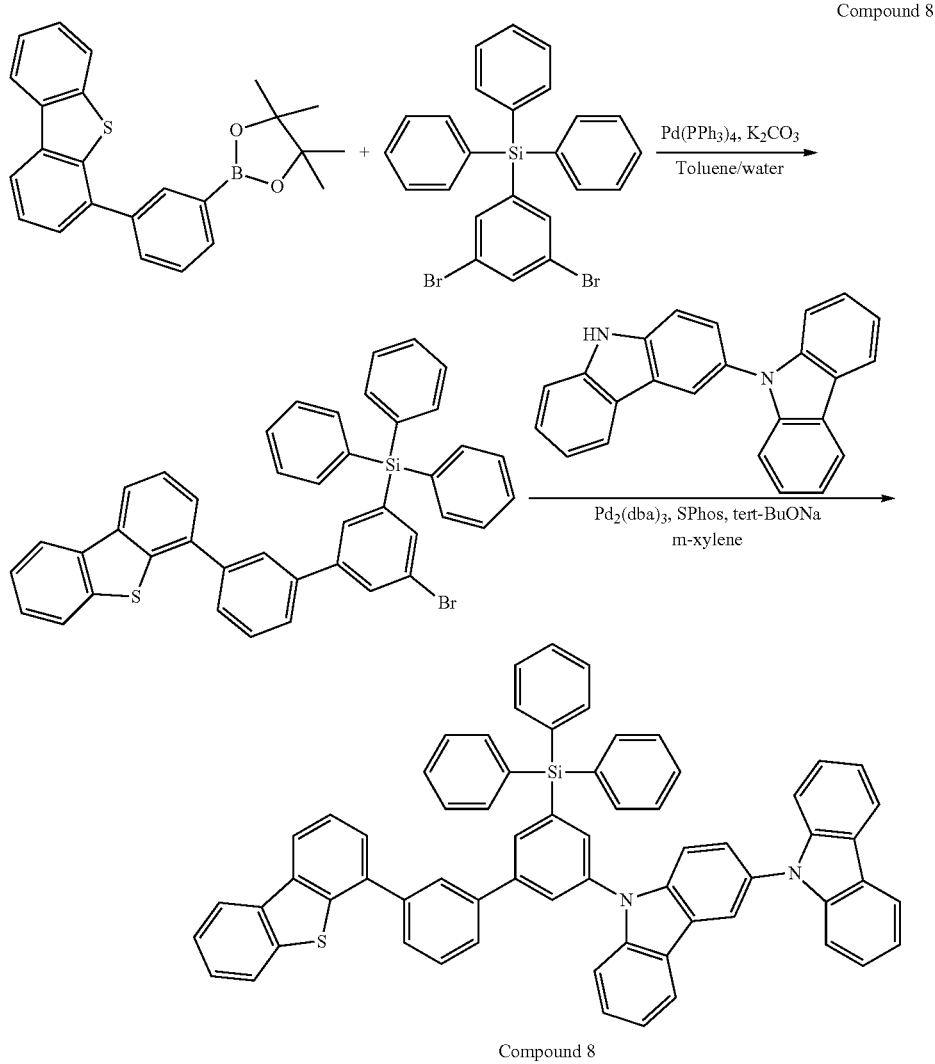

Compound 8

Synthesis of (5-bromo-3'-(dibenzo[b,d]thiophen-4-yl)-[1,1'-biphenyl]-3-yl)triphenylsilane A solution of 2-(3-(dibenzo[b,d]thiophen-4-yl)phenyl)-4,4,5,5-tetramethyl-1,3,2-dioxaborolane (2.00 g, 5.18 mmol), (3,5-dibromophenyl)triphenylsilane (5.12 g, 10.35 mmol), Pd(PPh$_3$)$_4$ (0.120 g, 0.104 mmol), K$_2$CO$_3$ (2.147 g, 15.53 mmol) in toluene (100 mL) and water (20 mL) was refluxed under nitrogen overnight. After cooling to room temperature, the organic phase was isolated, and the solvent was evaporated. The residue was purified by column chromatography on silica gel with hexane/DCM (2/1 v/v) as eluent to yield (5-bromo-3'-(dibenzo[b,d]thiophen-4-yl)-[1,1'-biphenyl]-3-yl)triphenylsilane (2.8 g, 80% yield) as a white solid.

Synthesis of Compound 8

A mixture of (5-bromo-3'-(dibenzo[b,d]thiophen-4-yl)-[1,1'-biphenyl]-3-yl)triphenylsilane (1.80 g, 2.67 mmol), 9H-3,9'-bicarbazole (0.89 g, 2.67 mmol), Pd$_2$(dba)$_3$ (0.049 g, 0.053 mmol), SPhos (0.044 g, 0.107 mmol), sodium tert-butoxide (0.77 g, 8.02 mmol) in m-xylene (100 mL) was refluxed at 150° C. overnight. After cooling to room temperature, it was passed through a short plug of Celite®. Upon evaporation of the solvent, the residue was purified by column chromatography on silica gel with hexane/DCM (3/1 to 2/1, v/v) as eluent to yield Compound 8 (2.2 g, 89% yield) as a white powder.

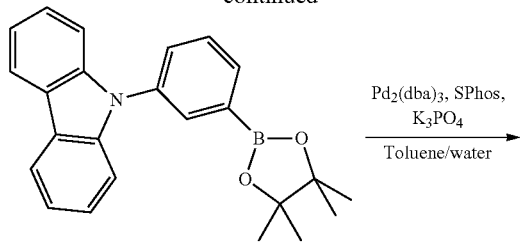

Compound 9

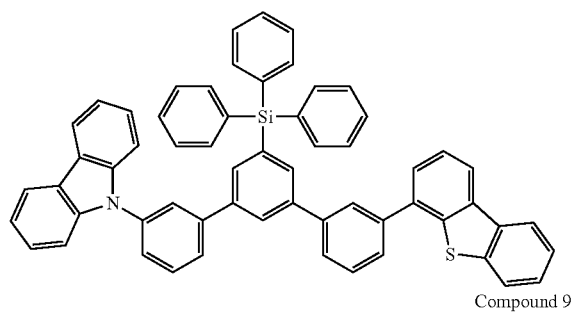

Compound 9

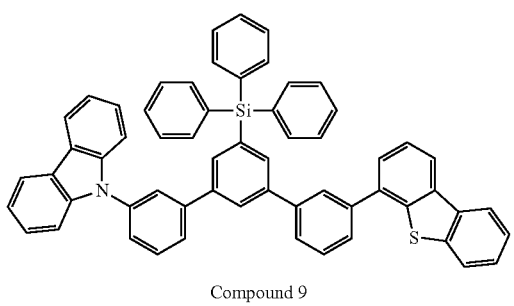

Compound 9

Synthesis Compound 9

A solution of (5-bromo-3'-(dibenzo[b,d]thiophen-4-yl)-[1,1'-biphenyl]-3-yl)triphenylsilane (2.180 g, 3.31 mmol), 9-(3-(4,4,5,5-tetramethyl-1,3,2-dioxaborolan-2-yl)phenyl)-9H-carbazole (1.346 g, 3.65 mmol), Pd$_2$(dba)$_3$ (0.061 g, 0.066 mmol), SPhos (0.054 g, 0.132 mmol) and K$_3$PO$_4$ (2.290 g, 9.94 mmol) toluene (100 mL) and water (2 mL) was refluxed under nitrogen overnight. After cooling to room temperature, the organic phase was isolated and the solvent is evaporated. The residue was purified by column chromatography on silica gel with hexane/DCM (3/1, v/v) as eluent to yield Compound 9 (2.1 g, 77% yield) as a white solid.

Compound 10

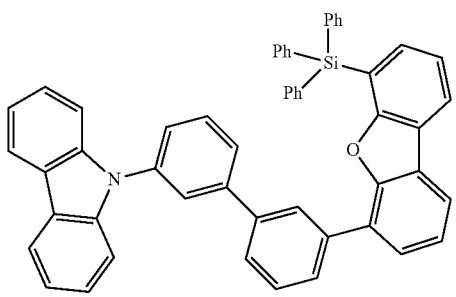

Compound 10

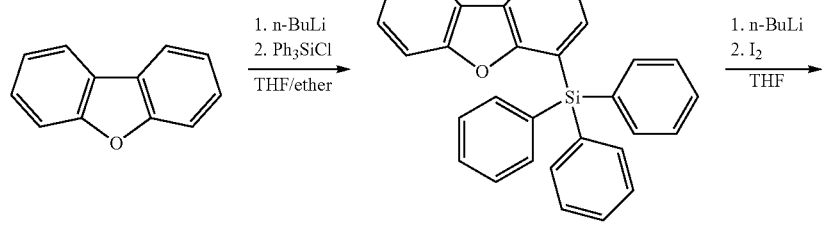

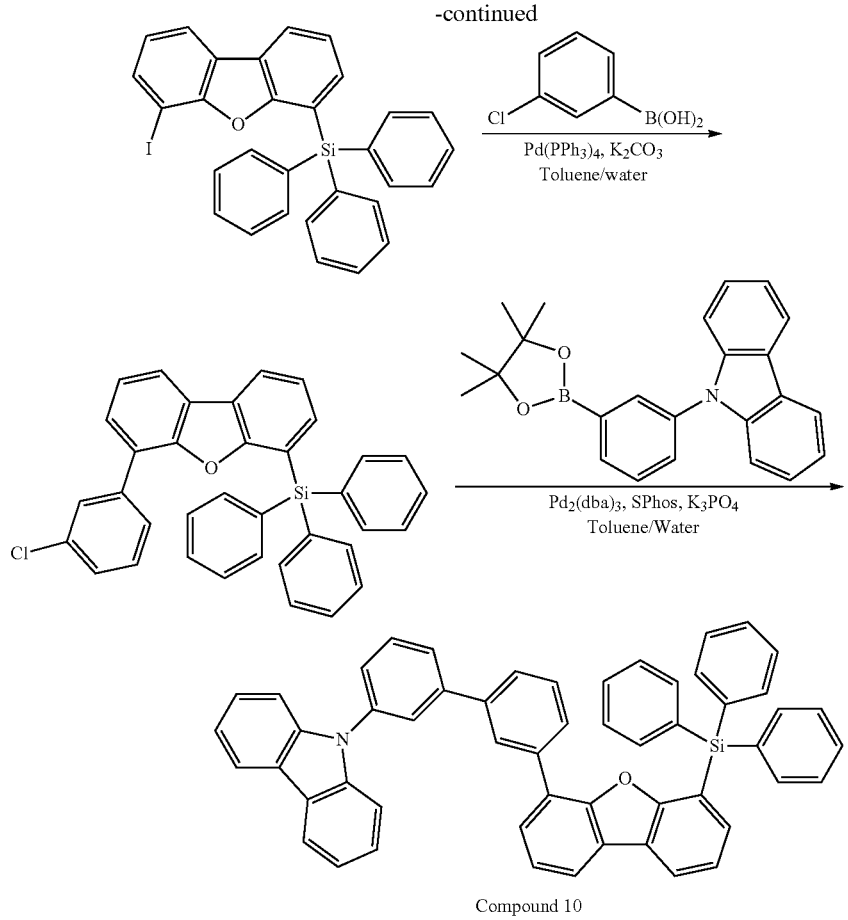

Compound 10

Synthesis of dibenzo[b,d]furan-4-yltriphenylsilane

Dibenzo[b,d]furan (5.00 g, 29.7 mmol) was dissolved in THF (150 mL), and cooled in the CO$_2$/i-PrOH bath. n-Butyllithium solution in hexane (2.5 M, 12.49 mL, 31.2 mmol) was added dropwise by syringe. After addition, it was stirred at room temperature for 2 hours, and cooled again in the CO$_2$/i-PrOH bath. Chlorotriphenylsilane (8.77 g, 29.7 mmol) in ether (50 mL) was added dropwise into the reaction solution. The reaction was gradually warmed to room temperature and stirred overnight. After evaporation of the solvent, the crude product was purified by column chromatography on silica gel with DCM/hexane (1/9, v/v) as eluent to yield dibenzo[b,d]furan-4-yltriphenylsilane (8.2 g, 65%) as a white solid.

Synthesis of (6-iododibenzo[b,d]furan-4-yl)triphenylsilane

Dibenzo[b,d]furan-4-yltriphenylsilane (9.80 g, 22.97 mmol) was dissolved in dry THF (100 mL) and cooled in the CO$_2$/i-PrOH bath. n-Butyllithium in hexane (2.5 M, 12.87 mL, 32.2 mmol) was added dropwise. It was warmed to room temperature, stirred for 4 hours, and cooled again in the CO$_2$/i-PrOH bath, and a solution of I$_2$ (8.63 g, 34 mmol) in ether (50 mL) was added dropwise. The reaction mixture was warmed to room temperature, stirred for 1 hour, and quenched with an aqueous solution of NaHSO$_3$ (10 wt %, 100 ml). It was diluted with saturated aqueous NaCl solution, extracted with EtOAc (50 mL×3 times). The organic extracts were combined, dried over anhydrous Na$_2$SO$_4$, and the solvent was evaporated. The residue was purified by column chromatography on silica gel with hexane/EtOAc (95/5 to 90/10, v/v) as eluent to yield (6-iododibenzo[b,d]furan-4-yl)triphenylsilane (7.8 g, 62%) as a white solid.

Synthesis of (6-(3-Chlorophenyl)dibenzo[b,d]furan-4-yl)triphenylsilane

A mixture solution of (6-Iododibenzo[b,d]furan-4-yl)triphenylsilane (6.60 g, 11.95 mmol), (3-chlorophenyl)boronic acid (2.80 g, 17.92 mmol), Pd(PPh$_3$)$_4$ (0.138 g, 0.119 mmol) and K$_2$CO$_3$ (3.30 g, 23.89 mmol) in toluene (100 mL) and water (15 mL) was refluxed under nitrogen for 24 hours. After cooling to room temperature, the organic phase was isolated and the solvent was evaporated. The residue was purified by column chromatography on silica gel with hexane/DCM (4/1, v/v) as eluent to yield (6-(3-chlorophenyl)dibenzo[b,d]furan-4-yl)triphenylsilane (3.7 g, 58%) as a white solid.

Synthesis of Compound 10

A solution of (6-(3-Chlorophenyl)dibenzo[b,d]furan-4-yl)triphenylsilane (2.130 g, 3.97 mmol), 9-(3-(4,4,5,5-tetramethyl-1,3,2-dioxaborolan-2-yl)phenyl)-9H-carbazole (1.464 g, 3.97 mmol), Pd$_2$(dba)$_3$ (40 mg, 44 mmol), SPhos (45 mg, 109 mmol), K$_3$PO$_4$ (2.283 g, 9.91 mmol) in toluene (100 ml) and water (1 ml) was stirred under nitrogen at 100° C. for 24 h. After evaporation of the solvent, the residue was purified by column chromatography on silica gel with hexane/DCM (7/3, v/v) as eluent to yield Compound 10 (2.3 g, 78%) as a white solid.

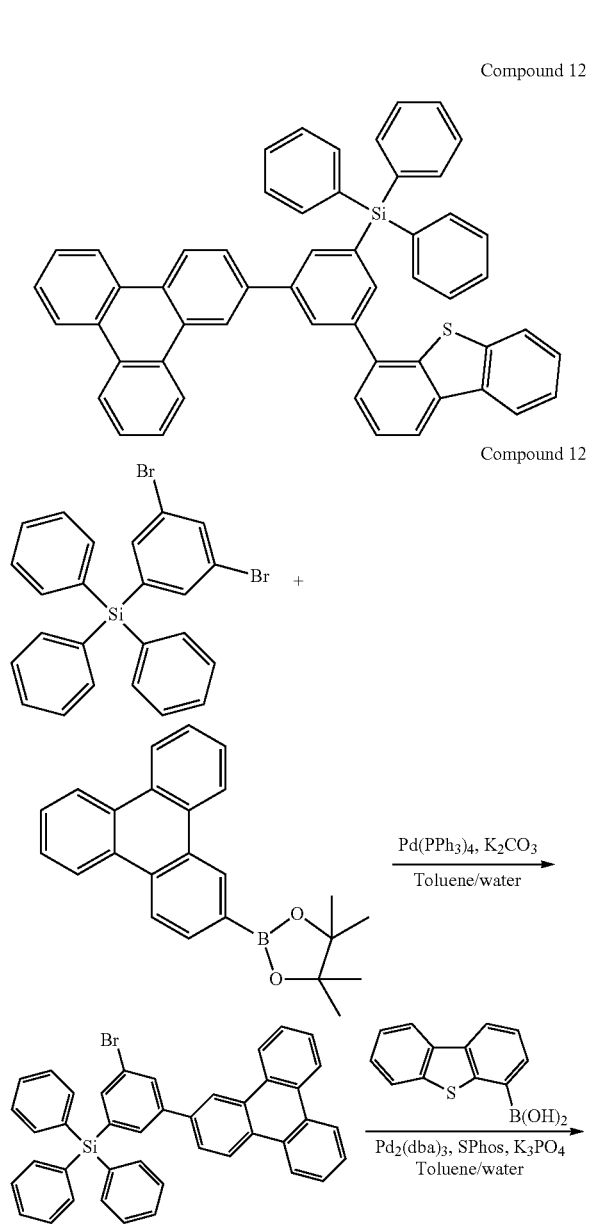

Compound 12

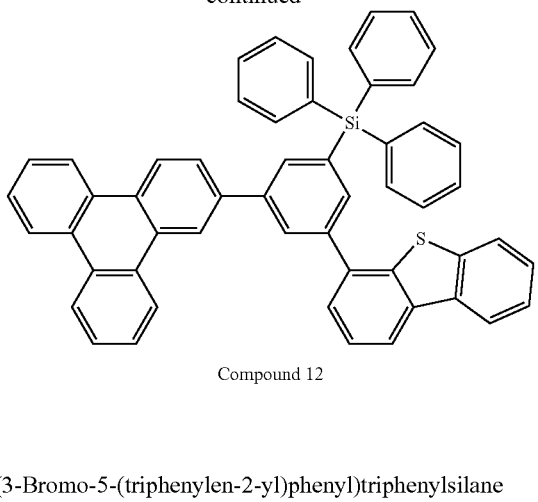

Compound 12

(3-Bromo-5-(triphenylen-2-yl)phenyl)triphenylsilane

A solution of (3,5-dibromophenyl)triphenylsilane (2.20 g, 4.45 mmol), 4,4,5,5-tetramethyl-2-(triphenylen-2-yl)-1,3,2-dioxaborolane (3.15 g, 8.90 mmol), Pd(PPh$_3$)$_4$ (0.051 g, 0.045 mmol) and K$_2$CO$_3$ (1.23 g, 8.90 mmol) in toluene (100 mL) and water (20 mL) was refluxed under nitrogen overnight. After cooling to room temperature, the organic phase was isolated, filtered through a short plug of Celite® and the solvent was evaporated. The residue was purified by column chromatography on silica gel with hexane/DCM (7/3, v/v) as eluent followed by recrystallization from the same solvent to yield (3-bromo-5-(triphenylen-2-yl)phenyl)triphenylsilane (1.50 g, 52%) as a white solid.

Synthesis of Compound 12

A solution of (3-bromo-5-(triphenylen-2-yl)phenyl)triphenylsilane (3.40 g, 5.30 mmol), dibenzo[b,d]thiophen-4-ylboronic acid (1.33 g, 5.83 mmol), Pd$_2$(dba)$_3$ (0.049 g, 0.053 mmol), SPhos (0.044 g, 0.106 mmol), K$_3$PO$_4$ (3.66 g, 15.90 mmol) in toluene (100 mL) and water (1 mL) was refluxed under nitrogen overnight. The hot reaction solution was filtered through a short plug of Celite® and the solvent was evaporated. The residue was purified by column chromatography on silica gel with hexane/DCM (7/3, v/v) as eluent to yield Compound 12 (2.70 g, 68%) as a white solid.

Compound 13

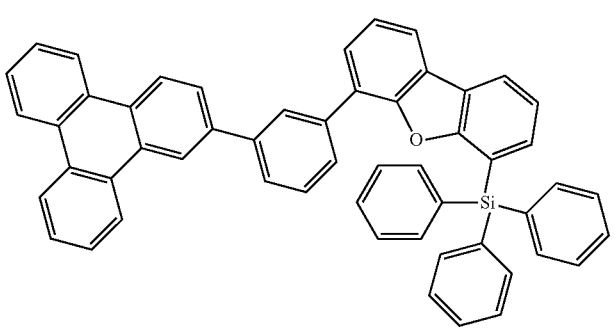

-continued

Compound 13

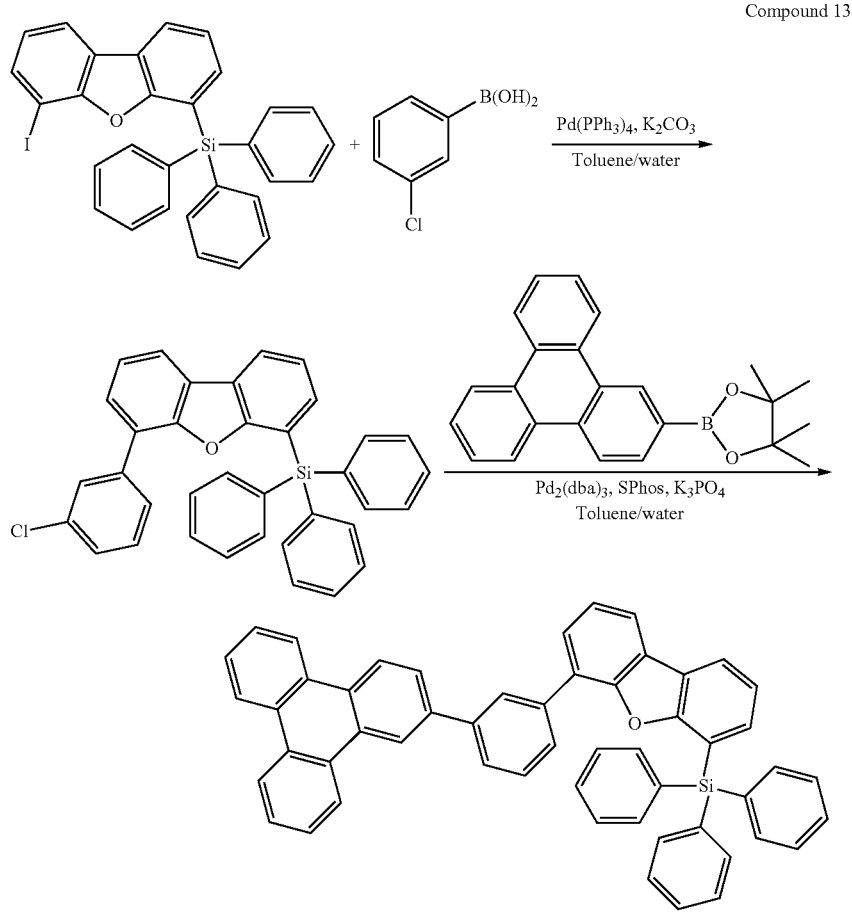

Compound 13

Synthesis of (6-(3-Chlorophenyl)dibenzo[b,d]furan-4-yl)triphenylsilane

A solution of (6-iododibenzo[b,d]furan-4-yl)triphenylsilane (5.00 g, 9.05 mmol), (3-chlorophenyl) boronic acid (1.7 g, 11.3 mmol), Pd(PPh$_3$)$_4$ (0.105 g, 0.091 mmol) and K$_2$CO$_3$ (2.502 g, 18.10 mmol) in toluene (75 mL) and water (10 mL) was refluxed under nitrogen for 48 h. The organic layer was separated and the solvent was evaporated. The residue was purified by column chromatography on silica gel with hexane (EtOAc (95/5, v/v) as eluent followed by recrystallization from the same solvent to yield (6-(3-chlorophenyl)dibenzo[b,d]furan-4-yl)triphenylsilane (1.0 g, 21%) as a white solid.

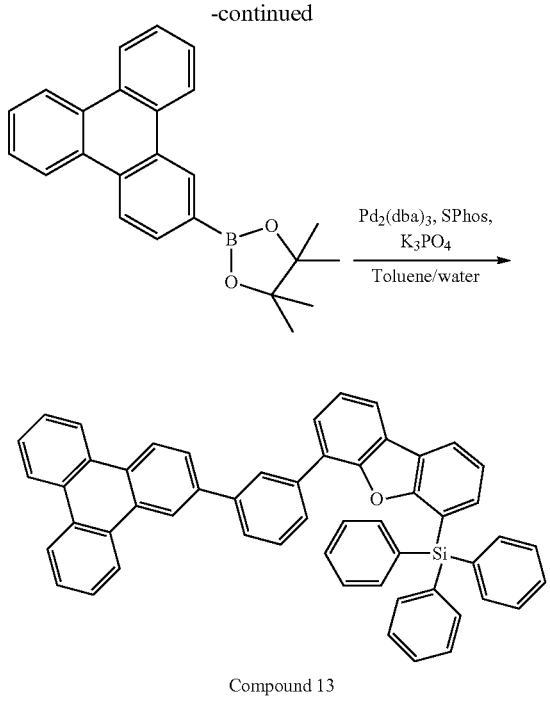

Compound 13

Synthesis of Compound 13

A solution of (6-(3-Chlorophenyl)dibenzo[b,d]furan-4-yl)triphenylsilane (1.63 g, 3.03 mmol), 4,4,5,5-tetramethyl-2-(triphenylen-2-yl)-1,3,2-dioxaborolane (1.12 g, 3.16 mmol), $Pd_2(dba)_3$ (0.090 g, xx mmol) and SPhos (0.10 g, 0.24 mmol) and $K_3PO_4$ (2.03 g, 8.8 mmol) in toluene (100 mL) and water (1 mL) was refluxed under nitrogen overnight. After cooling to room temperature, the solid was filtered of After evaporation off the solvent, the residue was purified by column chromatography on silica gel with hexane/DCM (7/3, v/v) as eluent followed by column chromatography on C18 column with acetonitrile as eluent to yield Compound 13 (1.6 g, 72%) as a white solid.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having the formula:

$L_1$-$L_2$-$L_3$       Formula I;

wherein $L_1$ is selected from the group consisting of carbazole, azacarbazole, triphenylene, aza-triphenylene and combinations thereof;

wherein $L_2$ is selected from the group consisting of phenyl, pyridine, pyrazine, triazine and combinations thereof;

wherein $L_3$ is selected from the group consisting of dibenzofuran, dibenzothiophene, azadibenzofuran, azadibenzothiophene, dibenzoselenophene, azadibenzoselenophene, and combinations thereof;

wherein at least one of $L_1$ to $L_3$ is substituted by at least one $SiAr_1Ar_2Ar_3$ group;

wherein $Ar_1$ to $Ar_3$ are independently selected from aryl or heteroaryl groups;

wherein each of $L_1$ to $L_3$ is optionally substituted with a group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof; and wherein any optional substitution on $L_1$ and $L_3$ can be fused to $L_1$ and $L_3$ respectively; and wherein any optional substitution on $L_2$ is unfused.

2. The compound of claim 1, wherein each of $L_1$ to $L_3$ is optionally substituted with a group selected from the group consisting of hydrogen, deuterium, aryl, heteroaryl, or combinations thereof.

3. The compound of claim 1, wherein each of $L_1$ to $L_3$ is substituted with hydrogen.

4. The compound of claim 1, wherein $L_1$ is selected from the group consisting of:

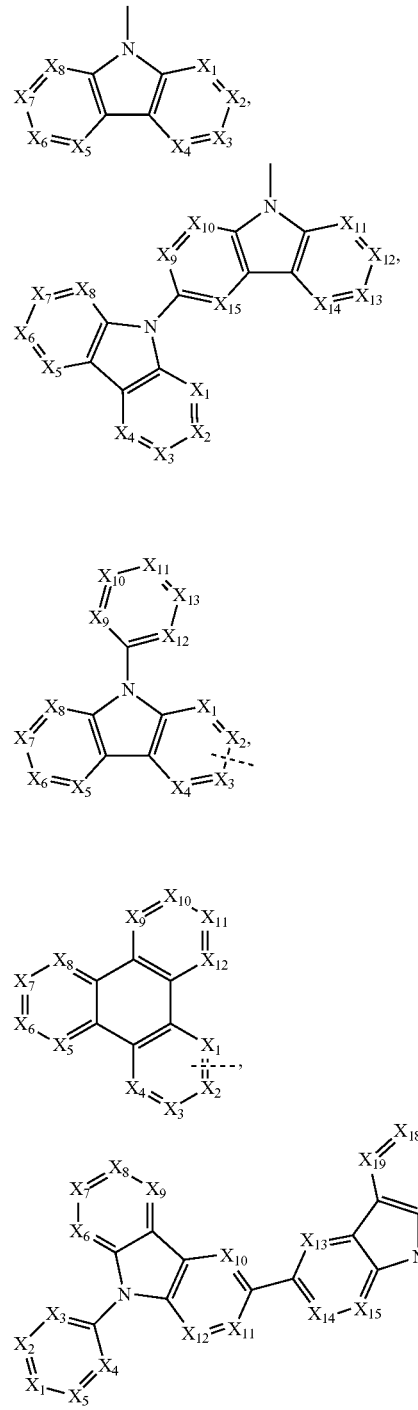

wherein $X_1$ to $X_{19}$ are independently CR or N;

and wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

5. The compound of claim 1, wherein $L_1$ is selected from the group consisting of:
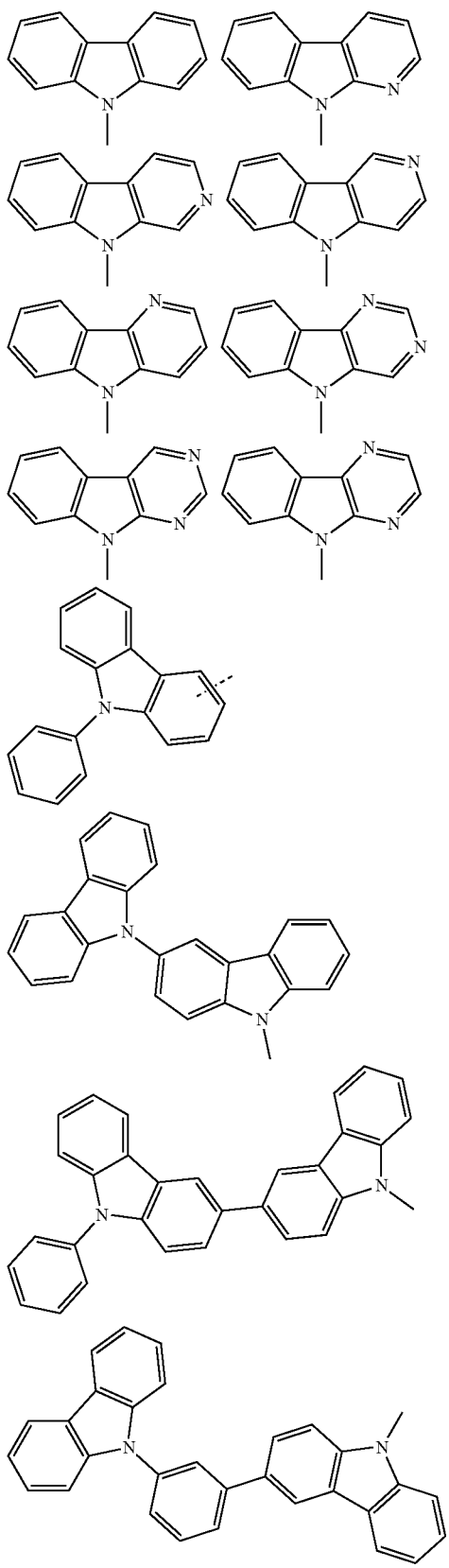
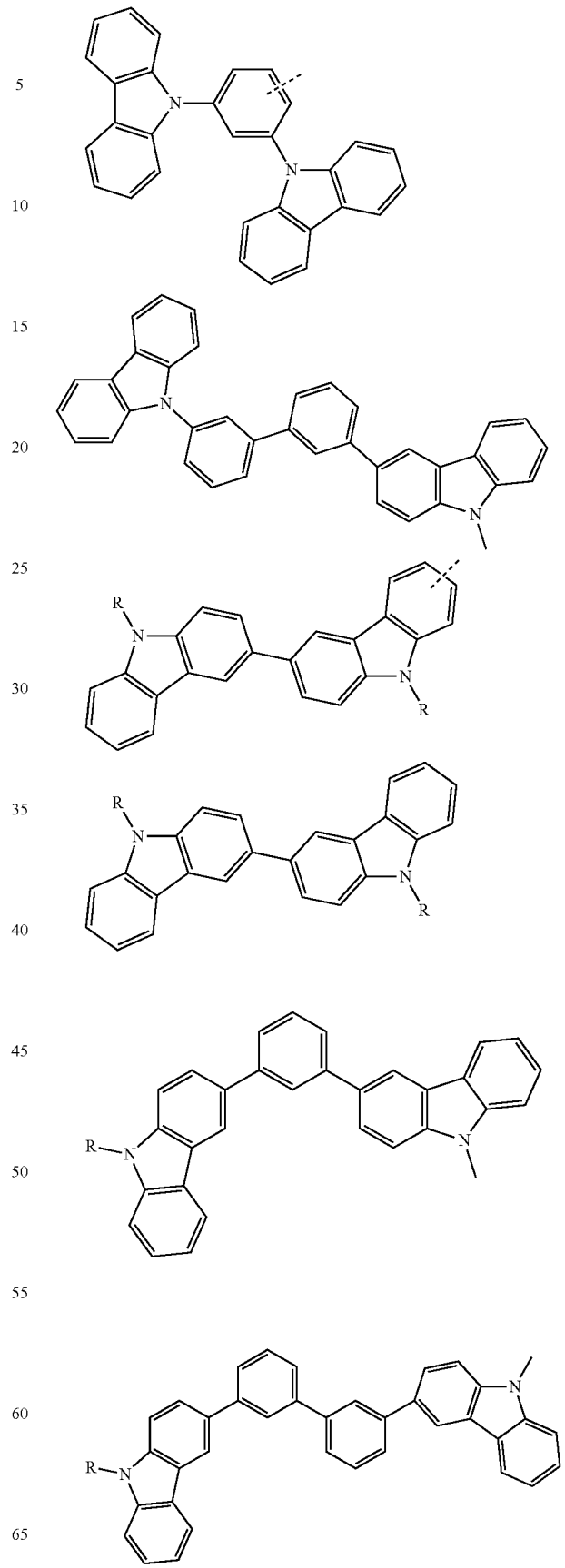

139
-continued

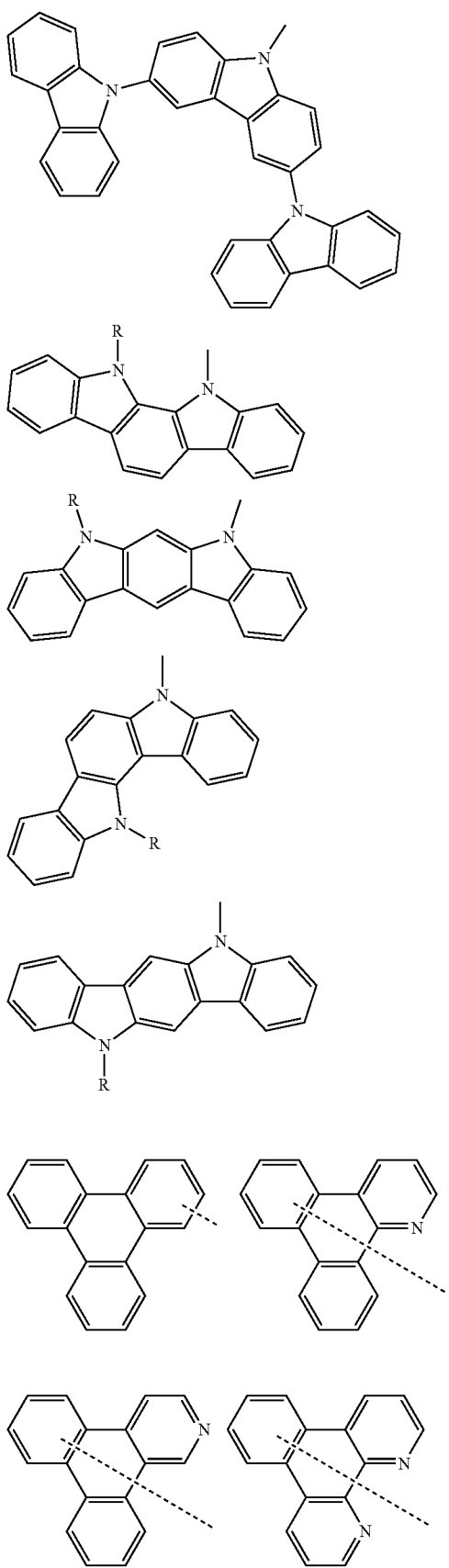

140
-continued

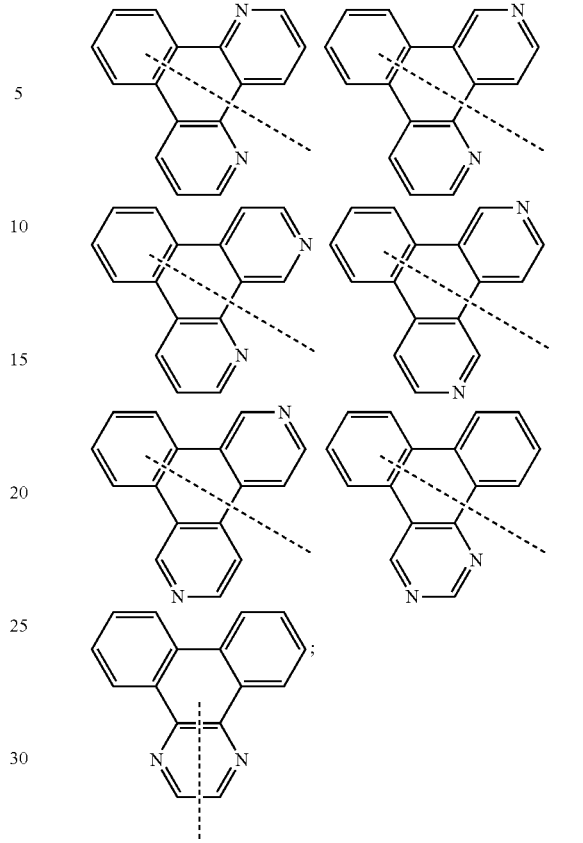

and wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof.

6. The compound of claim 1, wherein $L_2$ is selected from the group consisting of:

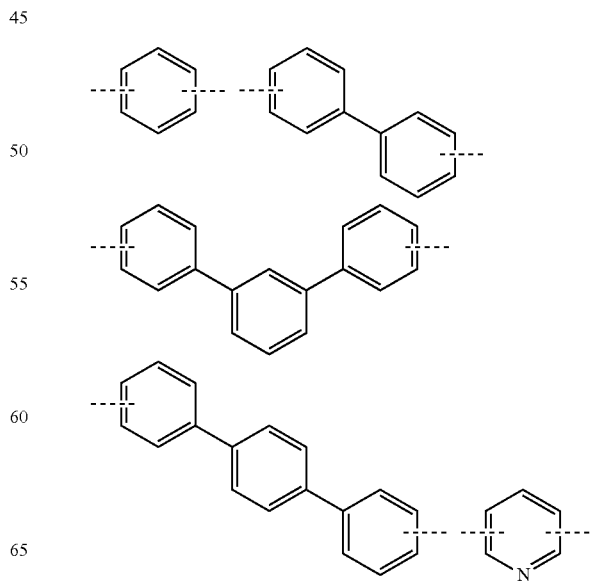

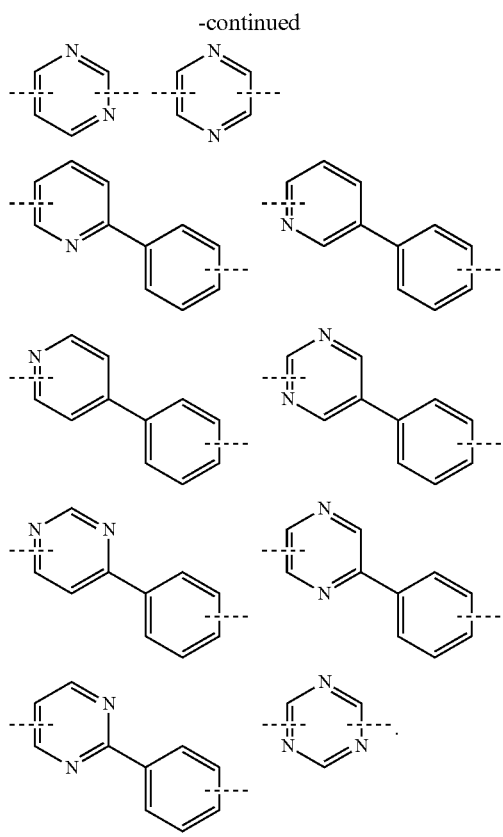

7. The compound of claim 1, wherein L₃ is selected from the group consisting of:

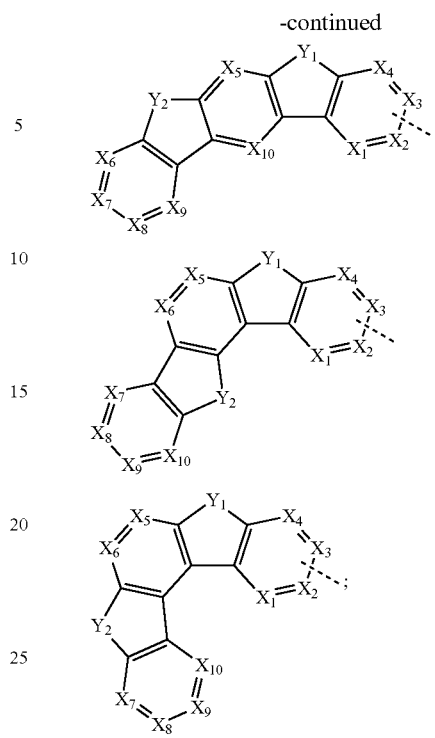

wherein $X_1$ to $X_{10}$ are independently CR or N;
wherein $Y_1$ and $Y_2$ are independently O, S, or Se;
and wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfonyl, sulfinyl, sulfonyl, phosphino, and combinations thereof.

8. The compound of claim 1, wherein L₃ is selected from the group consisting of:

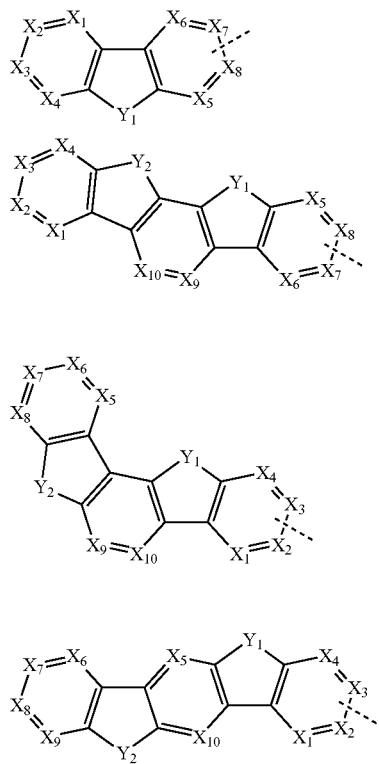

-continued

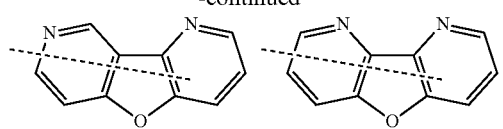

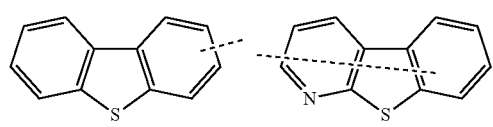

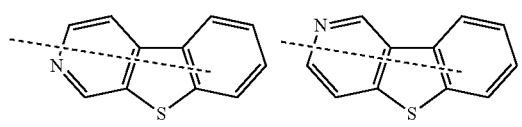

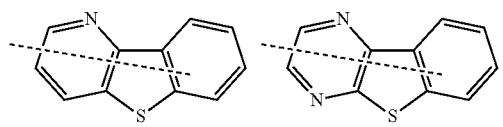

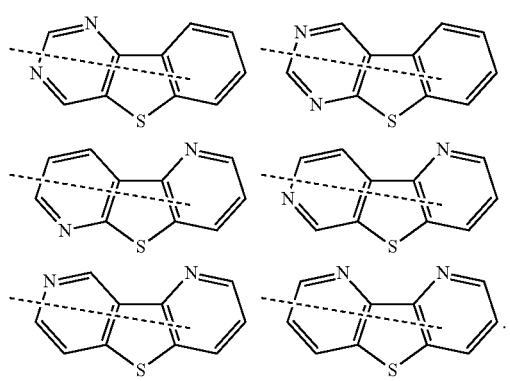

9. The compound of claim 1, wherein Ar$_1$ to Ar$_3$ are selected from the group consisting of phenyl, biphenyl, pyridyl, naphthyl, and combinations thereof.

10. The compound of claim 1, wherein Ar$_1$, Ar$_2$, and Ar$_3$ are phenyl.

11. The compound of claim 1, wherein L$_3$ contains dibenzothiophene.

12. The compound of claim 1, wherein L$_3$ contains dibenzofuran.

13. The compound of claim 1, wherein L$_2$ contains phenyl.

14. The compound of claim 1, wherein L$_2$ contains a biphenyl.

15. The compound of claim 1, wherein L$_2$ contains a terphenyl.

16. The compound of claim 1, wherein L$_1$ contains carbazole.

17. The compound of claim 1, wherein L$_1$ contains triphenylene.

18. The compound of claim 1, wherein the compound is selected from the group consisting of:

Compound 1

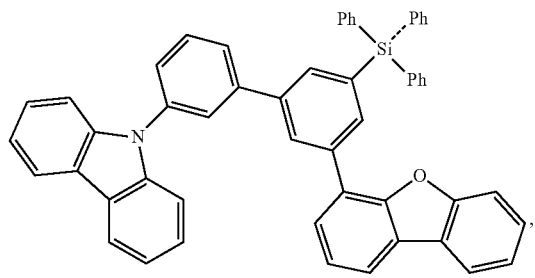

Compound 2

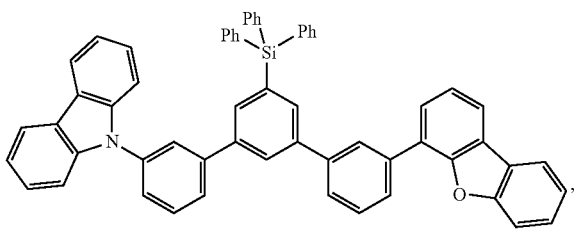

Compound 3

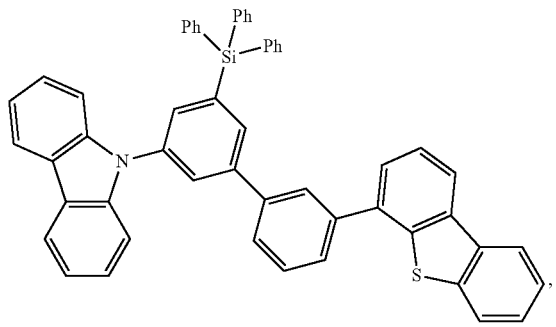

Compound 4

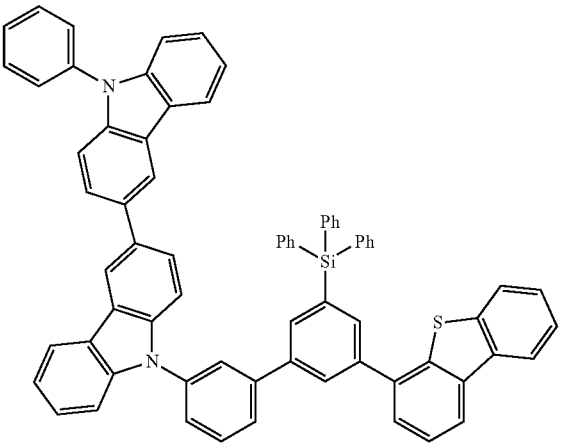

Compound 5
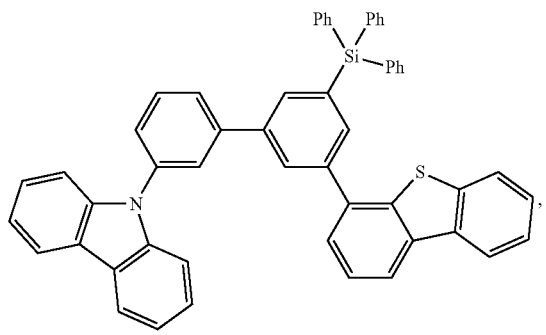
Compound 6
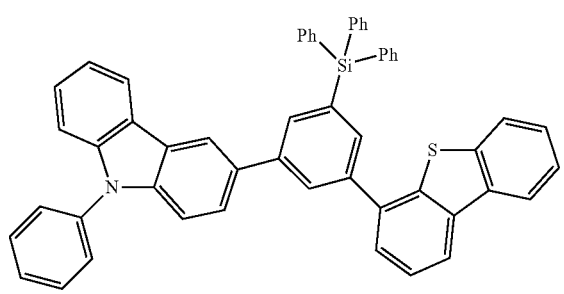
Compound 7
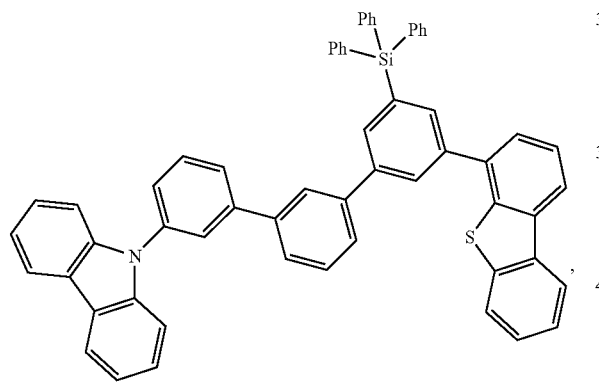
Compound 8
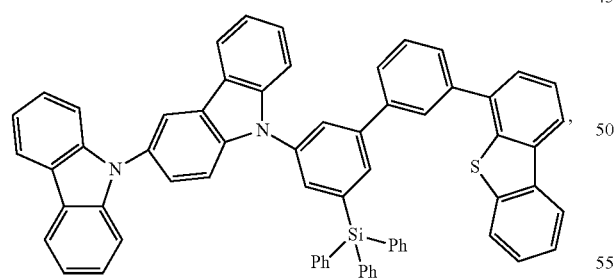
Compound 9
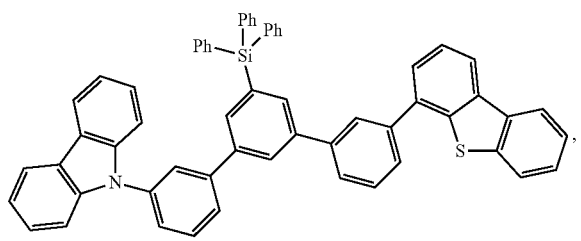
Compound 10
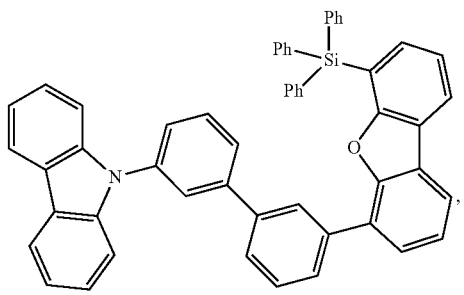
Compound 11
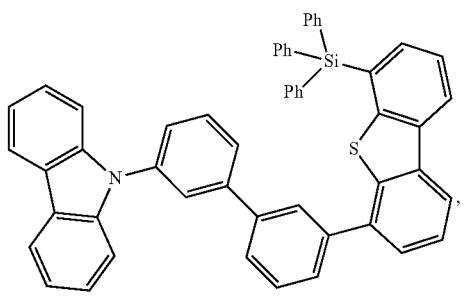
Compound 12
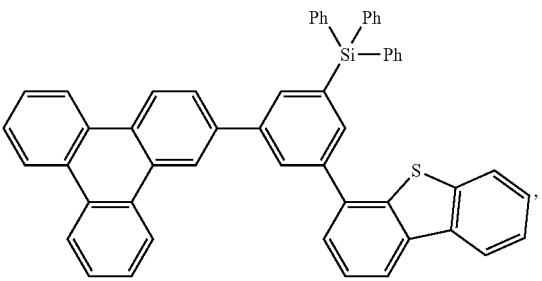
Compound 13
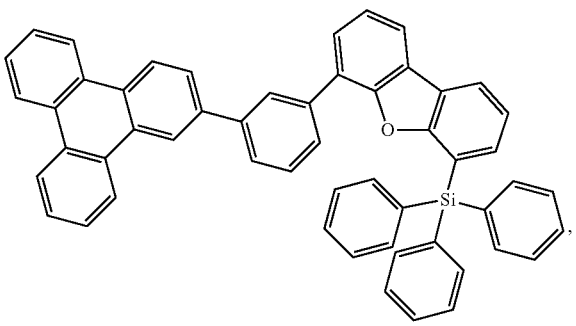

Compound 14
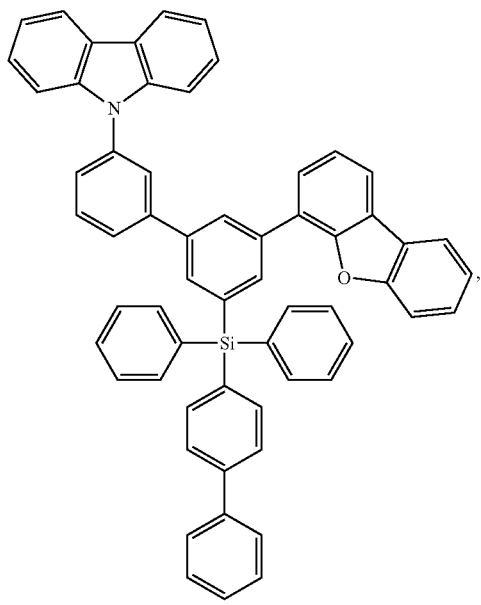
Compound 15
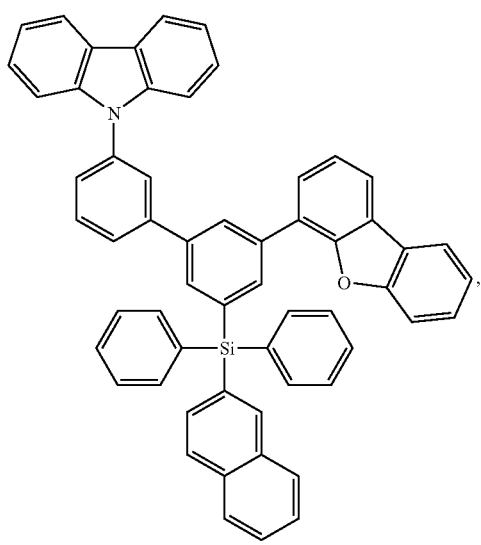
Compound 16
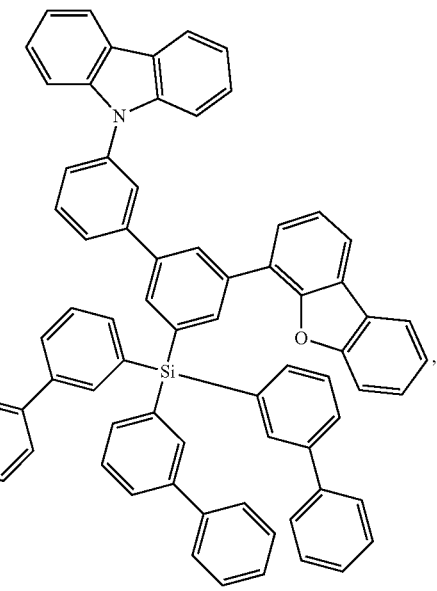
Compound 17
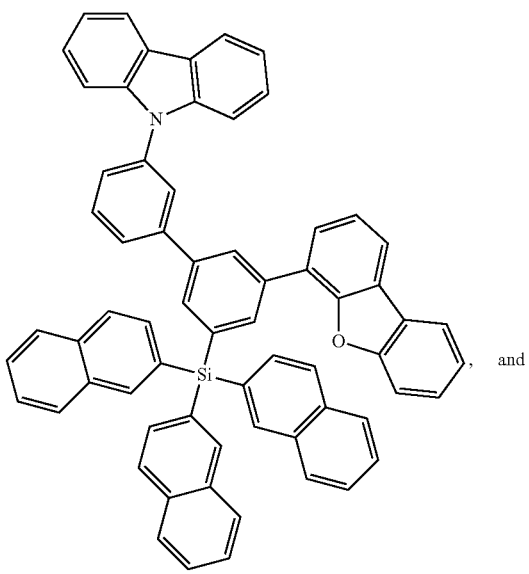
and Compound 18

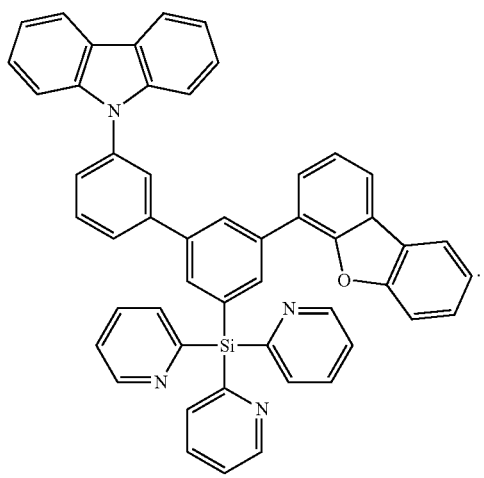

19. A first device comprising an organic light emitting device, further comprising:
an anode;
a cathode; and
an organic layer, disposed between the anode and the cathode, comprising a compound having the formula:

$L_1$-$L_2$-$L_3$  Formula I;

wherein $L_1$ is selected from the group consisting of carbazole, azacarbazole, triphenylene, aza-triphenylene and combinations thereof;
wherein $L_2$ is selected from the group consisting of phenyl, pyridine, pyrazine, triazine and combinations thereof;
wherein $L_3$ is selected from the group consisting of dibenzofuran, dibenzothiophene, azadibenzofuran, azadibenzothiophene, dibenzoselenophene, azadibenzoselenophene, and combinations thereof;
wherein at least one of $L_1$ to $L_3$ is substituted by at least one $SiAr_1Ar_2Ar_3$ group;
wherein $Ar_1$ to $Ar_a$ are independently selected from aryl or heteroaryl groups;
wherein each of $L_1$ to $L_3$ is optionally substituted with a group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof; and
wherein any optional substitution on $L_1$ and $L_3$ can be fused to $L_1$ and $L_3$ respectively; and
wherein any optional substitution on $L_2$ is unfused.

20. The first device of claim 19, wherein the organic layer is an emissive layer and the compound of Formula I is a host.

21. The first device of claim 20, further comprising a first dopant material that is an emissive dopant comprising a transition metal complex having at least one ligand or part of the ligand if the ligand is more than bidentate selected from the group consisting of:

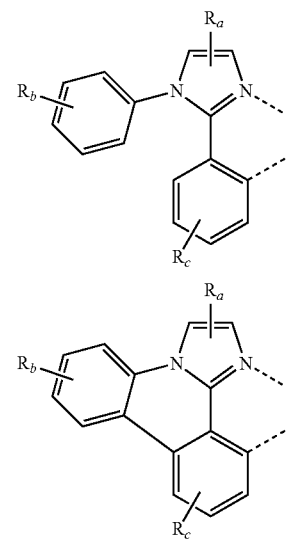

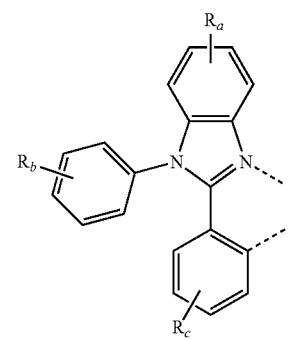

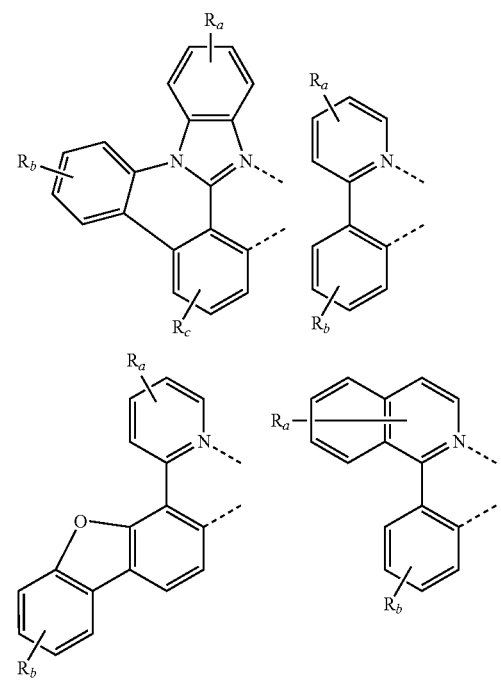

-continued

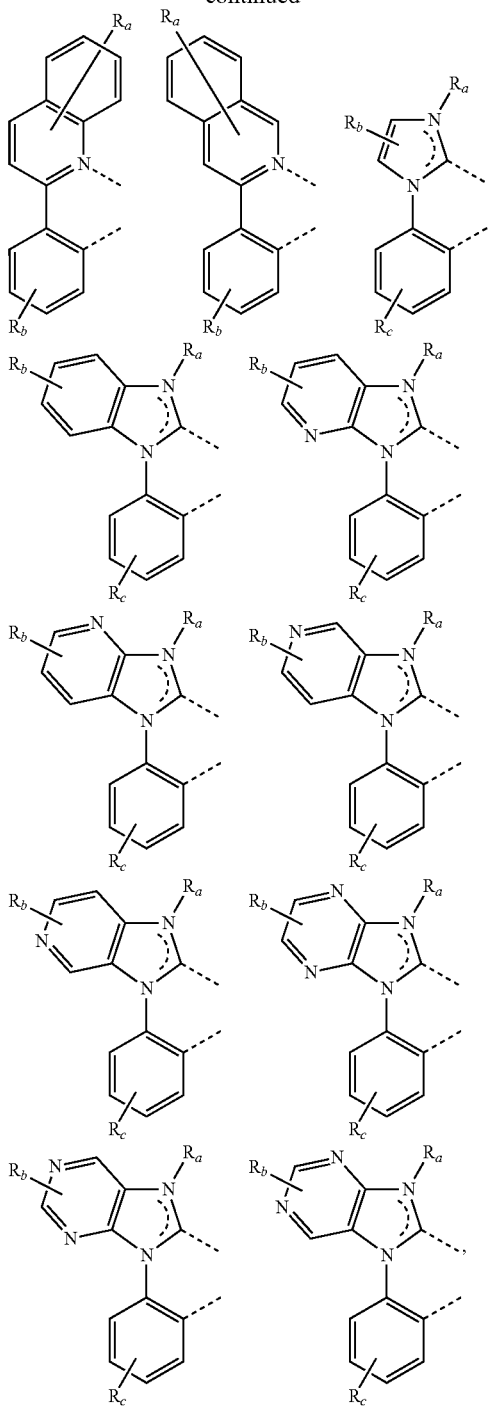

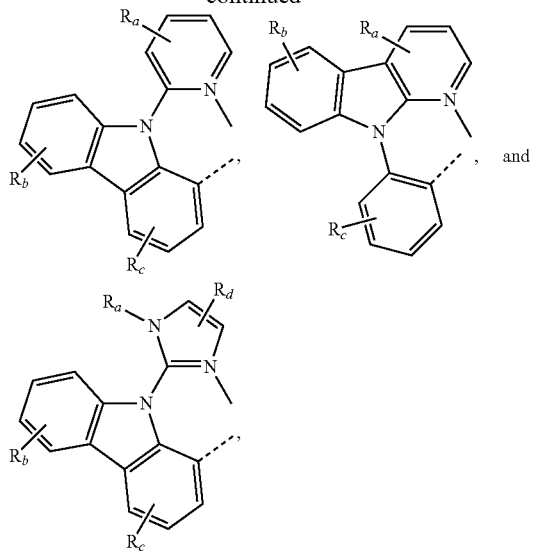

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl; heteroalkenyl, alkynyl, aryl, heteroaryl, acyl, carbonyl, carboxylic acids, ester, nitrile, isonitrile, sulfonyl, sulfonyl, sulfonyl, phosphino, and combinations thereof; and wherein two adjacent substituents of $R_a$, $R_b$, $R_c$, and $R_d$ are optionally joined to form a fused ring or form a multidentate ligand.

22. The first device of claim 19, wherein the organic layer is a non-emissive layer.

23. The first device of claim 19, wherein the organic layer is a first organic layer, and the device further comprises a second organic layer that is a non-emissive layer and the compound having Formula I is a material in the second organic layer.

24. The first device of claim 23, wherein the second organic layer is a blocking layer and the compound having Formula I is a blocking material in the second organic layer.

25. The first device of claim 19, wherein the first device is a consumer product.

26. The first device of claim 19, wherein the first device is an organic light-emitting device.

27. The first device of claim 19, wherein the first device comprises a lighting panel.

* * * * *

UNITED STATES PATENT AND TRADEMARK OFFICE
CERTIFICATE OF CORRECTION

PATENT NO.        : 9,184,399 B2
APPLICATION NO.   : 13/464122
DATED             : November 10, 2015
INVENTOR(S)       : Alexey Dyatkin, Lichang Zeng and Chuanjun Xia Page 1 of 1

It is certified that error appears in the above-identified patent and that said Letters Patent is hereby corrected as shown below:

In the Claims:

Claim 1, Column 135, Line 54 -- delete "sulfanyl" and insert -- sulfinyl --

Claim 5, Column 140, Line 41 -- delete the second recitation of "sulfanyl" and insert -- sulfinyl --

Claim 7, Column 142, Line 39 -- delete the first "sulfonyl" and insert -- sulfanyl --

Claim 19, Column 149, Line 46 -- delete "$Ar_a$" and insert -- $Ar_3$ --

Claim 19, Column 149, Line 55 -- delete the first "sulfonyl" and insert -- sulfinyl --

Claim 21, Column 152, Line 32 -- delete the first "sulfonyl" and insert -- sulfanyl --

Claim 21, Column 152, Line 32 -- delete the second "sulfonyl" and insert -- sulfinyl --

Signed and Sealed this
Sixteenth Day of February, 2016

Michelle K. Lee
*Director of the United States Patent and Trademark Office*